United States Patent
Qu et al.

(10) Patent No.: US 8,552,212 B2
(45) Date of Patent: Oct. 8, 2013

(54) CHIRAL PHOSPHORUS LIGANDS

(75) Inventors: Bo Qu, Brookfield, CT (US); Chris Hugh Senanayake, Brookfield, CT (US); Wenjun Tang, Shanghai (CN); Xudong Wei, Ridgefield, CT (US); Nathan K. Yee, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/504,146

(22) PCT Filed: Nov. 1, 2010

(86) PCT No.: PCT/US2010/054912
§ 371 (c)(1),
(2), (4) Date: May 23, 2012

(87) PCT Pub. No.: WO2011/056737
PCT Pub. Date: May 12, 2011

(65) Prior Publication Data
US 2012/0277455 A1  Nov. 1, 2012

Related U.S. Application Data

(60) Provisional application No. 61/258,417, filed on Nov. 5, 2009.

(51) Int. Cl.
*C07F 15/00* (2006.01)
*C07F 9/02* (2006.01)

(52) U.S. Cl.
USPC .......... 556/18; 568/12; 564/161; 560/155; 560/190; 556/20

(58) Field of Classification Search
USPC .......... 556/18, 20; 560/155, 190; 564/161; 568/12
See application file for complete search history.

(56) References Cited

U.S. PATENT DOCUMENTS

| 3,681,349 A | 8/1972 | Schwan et al. |
| 5,776,959 A | 7/1998 | Covey et al. |

(Continued)

FOREIGN PATENT DOCUMENTS

| DE | 10034623 A1 | 1/2002 |
| EP | 0645387 A1 | 3/1995 |

(Continued)

OTHER PUBLICATIONS

Abstract in English for DE10034623, Publication Date Jan. 31, 2002.

(Continued)

*Primary Examiner* — Porfirio Nazario Gonzalez
(74) *Attorney, Agent, or Firm* — Michael P. Morris; David L. Kershner

(57) ABSTRACT

The invention relates to a series of novel chiral phosphorus ligands of formulae (Ia) and (Ib): wherein R, 1-rR>4 and X are as defined herein. The invention also relates to chiral metal complexes prepared with these chiral phosphorus ligands. The chiral metal complexes are useful as catalysts for carrying out asymmetric hydrogenation.

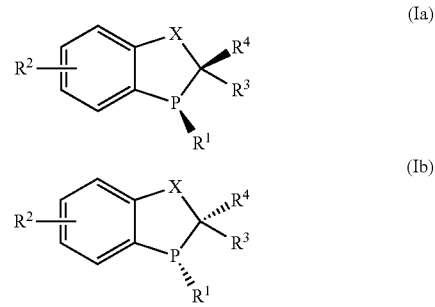

16 Claims, 1 Drawing Sheet

(56) References Cited

U.S. PATENT DOCUMENTS

| | | | |
|---|---|---|---|
| 5,811,422 | A | 9/1998 | Lam et al. |
| 8,114,868 | B2 | 2/2012 | Himmelsbach |
| 8,202,857 | B2 | 6/2012 | Claremon et al. |
| 8,242,111 | B2 | 8/2012 | Claremon et al. |
| 2007/0208001 | A1 | 9/2007 | Zhuo et al. |
| 2009/0264650 | A1 | 10/2009 | Cho et al. |
| 2010/0016164 | A1 | 1/2010 | Hino et al. |
| 2010/0041637 | A1 | 2/2010 | Claremon et al. |
| 2010/0197675 | A1 | 8/2010 | Claremon et al. |
| 2010/0256363 | A1 | 10/2010 | Xu |
| 2010/0324045 | A1 | 12/2010 | Claremon et al. |
| 2010/0331320 | A1 | 12/2010 | Renz et al. |
| 2011/0009402 | A1 | 1/2011 | Himmelsbach |
| 2011/0015157 | A1 | 1/2011 | Claremon et al. |
| 2011/0021512 | A1 | 1/2011 | Claremon et al. |
| 2011/0034455 | A1 | 2/2011 | Claremon et al. |
| 2011/0053943 | A1 | 3/2011 | Claremon et al. |
| 2011/0071139 | A1 | 3/2011 | Claremon et al. |
| 2011/0098320 | A1 | 4/2011 | Claremon et al. |
| 2011/0105504 | A1 | 5/2011 | Claremon et al. |
| 2011/0112062 | A1 | 5/2011 | Claremon et al. |
| 2011/0112082 | A1 | 5/2011 | Claremon et al. |
| 2011/0124635 | A1 | 5/2011 | Claremon et al. |
| 2011/0136821 | A1 | 6/2011 | Claremon et al. |
| 2011/0190262 | A1 | 8/2011 | Himmelsbach et al. |
| 2011/0263582 | A1 | 10/2011 | Claremon et al. |
| 2011/0263583 | A1 | 10/2011 | Claremon et al. |
| 2011/0263584 | A1 | 10/2011 | Claremon et al. |
| 2011/0269957 | A1 | 11/2011 | Fandrick et al. |
| 2011/0312950 | A1 | 12/2011 | Eckhardt et al. |
| 2012/0040973 | A1 | 2/2012 | Claremon et al. |
| 2012/0108578 | A1 | 5/2012 | Himmelsbach et al. |
| 2012/0184549 | A1 | 7/2012 | Himmelsbach |
| 2012/0190675 | A1 | 7/2012 | Himmelsbach |
| 2012/0208804 | A1 | 8/2012 | Claremon et al. |
| 2012/0232050 | A1 | 9/2012 | Claremon et al. |
| 2012/0277149 | A1 | 11/2012 | Hamilton et al. |
| 2012/0277455 | A1 | 11/2012 | Qu et al. |

FOREIGN PATENT DOCUMENTS

| | | |
|---|---|---|
| EP | 0928789 A1 | 7/1999 |
| EP | 1156049 A1 | 11/2001 |
| EP | 1801098 A1 | 6/2007 |
| EP | 1852425 A1 | 11/2007 |
| EP | 1864971 A1 | 12/2007 |
| JP | 2007254409 A | 10/2007 |
| WO | 9614297 A1 | 5/1996 |
| WO | 0009107 A2 | 2/2000 |
| WO | 0113917 A1 | 3/2001 |
| WO | 0144200 A2 | 6/2001 |
| WO | 03057673 A1 | 7/2003 |
| WO | 2004056745 A2 | 7/2004 |
| WO | 2004094375 A2 | 11/2004 |
| WO | 2005108361 A1 | 11/2005 |
| WO | 2005116002 A2 | 12/2005 |
| WO | 2006002349 A1 | 1/2006 |
| WO | 2006014357 A1 | 2/2006 |
| WO | 2006017443 A2 | 2/2006 |
| WO | 2006024627 A2 | 3/2006 |
| WO | 2006024628 A1 | 3/2006 |
| WO | 2006031715 A2 | 3/2006 |
| WO | 2006040329 A1 | 4/2006 |
| WO | 2006049952 A1 | 5/2006 |
| WO | 2006104280 A1 | 10/2006 |
| WO | 2007061661 A2 | 5/2007 |
| WO | 2007081570 A2 | 7/2007 |
| WO | 2007101270 A1 | 9/2007 |
| WO | 2007103719 A2 | 9/2007 |
| WO | 2007124254 A2 | 11/2007 |
| WO | 2007124329 A1 | 11/2007 |
| WO | 2007124337 A1 | 11/2007 |
| WO | 2007127693 A1 | 11/2007 |
| WO | 2007127763 A2 | 11/2007 |
| WO | 2008024497 A2 | 2/2008 |
| WO | 2008046758 A2 | 4/2008 |
| WO | 2008059948 A1 | 5/2008 |
| WO | 2008106128 A2 | 9/2008 |
| WO | 2009017664 A1 | 2/2009 |
| WO | 2009017671 A1 | 2/2009 |
| WO | 2009020140 A1 | 2/2009 |
| WO | 2009061498 A1 | 5/2009 |
| WO | 2009075835 A1 | 6/2009 |
| WO | 2009088997 A1 | 7/2009 |
| WO | 2009094169 A1 | 7/2009 |
| WO | 2009102428 A2 | 8/2009 |
| WO | 2009102460 A2 | 8/2009 |
| WO | 2009108332 A1 | 9/2009 |
| WO | 2009117109 A1 | 9/2009 |
| WO | 2009131669 A2 | 10/2009 |
| WO | 2009134384 A1 | 11/2009 |
| WO | 2009134387 A1 | 11/2009 |
| WO | 2009134392 A1 | 11/2009 |
| WO | 2009134400 A1 | 11/2009 |
| WO | 2010010150 A1 | 1/2010 |
| WO | 2010010157 A2 | 1/2010 |
| WO | 2010011314 A1 | 1/2010 |
| WO | 2010089303 A1 | 8/2010 |
| WO | 2010091067 A2 | 8/2010 |
| WO | 2010104830 A1 | 9/2010 |
| WO | 2010127237 A2 | 11/2010 |
| WO | 2010141424 A1 | 12/2010 |
| WO | 2011002910 A1 | 1/2011 |
| WO | 2011011123 A1 | 1/2011 |
| WO | 2011031979 A1 | 3/2011 |
| WO | 2011056737 A1 | 5/2011 |
| WO | 2011159760 A1 | 12/2011 |
| WO | 2011161128 A1 | 12/2011 |
| WO | 2012059416 A1 | 5/2012 |

OTHER PUBLICATIONS

Aluri, B.R. et al., "Bulky n-Substituted 1,3-Benzazaphospholes: Access via Pd-Catalyzed C-N. and C-P Cross Coupling, Lithiation, and Conversion to Novel P=C PtBu2 Hybrid Ligands". Inorganic Chemistry, 2008, 47, p. 6900-6912.

Aluri, B.R. et al., "Sterically and Polarity-Controlled Reactions of tBuLi with P=CH-NR Heterocycles: Novel Heterocyclic P-and P,O-Ligands and Preliminary Tests in Transition-Metal Catalysis", Chem. Eur. Journal, vol. 14, 2008, p. 4328-4335.

ChemAbstract—Accession #: 1969:68280. Maillard, J. et al., "Spiroheterocyclic cycloalkane compounds II. Synthesis of 6-substituted-tetrahydro-2H-1, 3-oxazine-2-ones." Chima Therapeutica, 3(5), 1968, pp. 321-324.

ChemAbstract—Accession #: 1978:563520. Slyusarenko, E.I., et al., Syntheses based on thionylamides. IV. 2-alkoxy-5,6-dihydro-1,3-oxazines. Zhurnal Organicheskoi Chimii, 14(5), 1979, p. 1093.

ChemAbstract—Accession #: 1983:595067. Saitkulova, F.G. et al., "Syntheses involving bromozinc alcholates of carboxylic acid esters". Khimiya Elementoorganicheskikh Soedinii, vol. 1982, 1982, pp. 22-26.

ChemAbstract—Accession #: 1983:89280. Lapkin, I.I. et al., "Synthesis of 1,3-oxazine-2,4-diones." Zhurnal Organicheskoi Khimii, vol. 18, No. 11, 1982, p. 2468.

ChemAbstract—Accession No. 2007:1110441 Abstract, Chemical Abstract Service, Columbus, Ohio, Fukushima, H. et al., "Preparation of imidazolidinone derivatives as 11.beta.-HSD1 inhibitors". JP20072544-9 (Taisho Pharmaceutical Co. Ltd., Japan, Oct. 4, 2007. (Attached is a machine translation of the ChemAbstract and a Derwent World Patents Index file record).

ChemAbstract: CAS: 150:214405, Accession #: 2009:140024. Claremon, D.A., et al., Preparation of 1,3-oxazinan-2-one dervatives as inhibitors of 11-beta-hydroxysteroid dehydrogenase type1. 2009.

Donohoe, T.J. et al., "Stereoselectivity in the double reductive alkylation of pyrroles: synthesis of cis-3,4-disubstituted pyrrolidines". Chemical Communications, vol. 1999, No. 2, Feb. 1, 1999, p. 141-142.

Evans, B.E. et al., "Orally active, nonpeptide osytocin antagonists". Journal of Medicinal Chemistry, American Chem. Soc., Vo. 35, No. 21, Oct. 15, 1992, p. 3919-3927.

Fandrick, D.R. et al., "Copper Catalyzed Asymmetric Propargylation of Aldehydes". JACS Communications, Published on Web May 18, 2010, J. Am. Chem. Soc., vol. 132, No. 22, 2010, p. 7600,7601.

Goubet, F. et al., "Conversion of a Thiohydantoin to the Corresponding Hydantoin via a Ring-Opening/Ring Closure Mechanism". Tetrahedron Letters, Elsevier, Amsterdam, vol. 37. No. 43, Oct. 21, 1996. p. 7727-7730.

Harno, E. et al., "Will treating diabetes with 11-beta-HSD1 inhibitors affect the HPA axis?" Trends in Endocrinology and Metabolism, Elsevier Science Publishing, NY, NY, USm, vol. 21, No. 10, Oct. 1, 2010, pp. 619-627.

International Search Report and Written Opinion for PCT/US2010/054912 mailed Mar. 16, 2011.

Kashima, C. et al., "Preparation of N-Aryl-2,4-diaminopentanes by the Ring Opening Reaction of 1-Aryl-3,4,5,6-tetradydro-2-(1H)pyrimidinones". Journal of Heterocyclic Chemistry, vol. 18, 1981, p. 1595-1596.

Lightburn, T.E. et al., "Catalytic Scaffolding Ligands: An Efficient Strategy for Direction Reactions". JACS Communications, Published on Web May 25, 2008, Journal American Chem. Soc., vol. 130, No. 29, 2008, p. 9210-9211.

Muehlstadt, M. et al., "Cyclisation reactions of beta,gamma-unsaturated derivatives of carbonis acid. IX" Journal Fuer Praktische Chemi, vol. 328, 1986, p. 163-172.

Rosenstock, J. et al., "The 11-beta-hydroxysteroid Dehydrogenase Type 1 inhibitor INCB13739 Improves Hyperglycemia in Patients with Type 2 Diabetes Inadequately Controlled by Metformin Monotherapy." Diabetes Care, vol. 33, No. 7, Jul. 2010, pp. 1516-1522.

Schoellkopf, U. et al., "Umsetzungen Alphametallierter Isocyanide Mit Eigigen 1,3-Dipolen" English: "Reactions of alpha-metalated osicyanidews with some 1,3-dipoles", Liebigs Annalen Der Chemie, Verlag Chemi, GmbH, Weinheim, DE, vol. 4, Jan. 1, 1980, p. 600-610.

Senanayake, C. Presentation: "Timely Chemical Process Research is a Critical Part for Efficient Drug Development". 4th Siegfried Symposium, Sep. 23, 2010, p. 1-91, Retrieved from internet: URL: http://www.siegfried/ch/fileadmin/User2/Bilder/Fotogalerien/Symposium_2010/Award_Talk_Senanayake.pdf. Retrieved on Feb. 23, 2010.

Shibata, I. et al., "Cycloaddition of Oxetanes with Heterocumulenes Catalyzed by Organotin Iodine-Lewis Base Complex". Journal of Heterocyclic Chemistry, vol. 24, 1987, p. 361-363.

Tadayyon M. et al., "Insulin sensitisation in the treatment of Type 2 diabetes." Expert Opinion on Investigational Drugs, Ashley Publications, Ltd., London, GB, vol. 12, n. 3, Mar. 1, 2003, pp. 307-324.

Tamaru, Y. et al., "Palladium (2+)-Catalyzed Intramolecular Aminocarbonylation of 3-Hydroxy-4-pentenylamines and 4-Hydroxy-5-hexenylamines". Journal Organic Chemistry, vol. 53, No. 24, 1988, p. 5731-5741.

Tamaru, Y. et al., "Urea as the Most Reactive and Versatile Nitrogen Nucleophile for the Palladium (2+)-Catalyzed Cyclization of Unsaturated Amines," J. Am. Chem. Soc., 1988, 110, 3994-4002.

Tang, W. et al., "Novel and Efficient Chiral Bisphosphorus Ligands for Rhodium-Catalyzed Asymmetric Hydrogenation". Organic Letters, 2010, vol. 12, No. 5, p. 1104-1107.

Tang, W. et al., "Novel, Tunable, and Efficient Chiral Bisdihydrobenzooxaphosphole Ligands for Asymmetric Hydrogenation". Organic Letters, 2010, vol. 12, No. 1., p. 176-179.

Worthy, A.D. et al., "Regioselective Hydroformylation of Sulfonamides using a Scaffolding Ligand". Organic Letters, 2009, vol. 11, No. 13—p. 2764-2767.

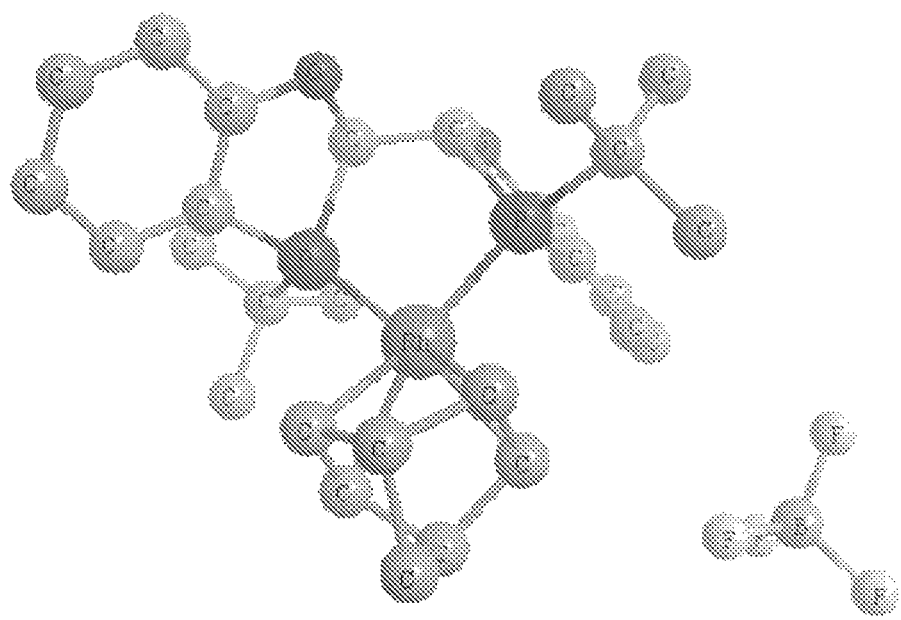

CHIRAL PHOSPHORUS LIGANDS

FIELD OF THE INVENTION

The present invention relates to a series of novel chiral phosphorus ligands and their metal complexes as catalysts for applications in asymmetric hydrogenation. More particularly, the present invention relates to the transition metal complexes of these novel phosphine ligands and their use as catalysts in asymmetric hydrogenation.

BACKGROUND OF THE INVENTION

The increasing demand to produce enantiomerically pure pharmaceuticals, agrochemicals, flavors, and other fine chemicals has advanced the field of asymmetric catalytic technologies. Development of efficient asymmetric metal-catalyzed transformations has played a central role for the advancement of asymmetric catalysis (Jacobsen, E. N., Pfaltz, A., Yamamoto, H., Eds., Comprehensive Asymmetric Catalysis, Springer, Berlin, 1999; Ojima, I., Ed, *Catalytic Asymmetric Synthesis*, VCH, New York, 1993; and Noyori, R. *Asymmetric Catalysis In Organic Synthesis*, John Wiley & Sons, Inc, New York, 1994). Among most successful transformations are asymmetric hydrogenation, asymmetric epoxidation and dihydroxylations, which were awarded Nobel Prizes in 2001 for their efficiency, simplicity, and practicality. Chiral ligand design has become and will continue to be of great importance for developing new efficient asymmetric metal-catalyzed reactions.

Asymmetric hydrogenation utilizing molecular hydrogen to reduce prochiral olefins, ketones, and imines has become one of most efficient methods for constructing chiral compounds. It also accounts for the major asymmetric catalytic transformation at commercial scales. Development of efficient chiral phosphorus ligands is essential for the success of asymmetric hydrogenation. Known chiral phosphorus ligands in this field include Knowles' DIPAMP [Knowles, W. S. *Acc. Chem. Res.* 1983, 16, 106], Kagan's DIOP [Kagan et al, *J. Am. Chem. Soc.* 1972, 94, 6429], Noyori's BINAP [Noyori, R. *Chem. Soc. Rev.* 1989, 18, 187], Burk's Duphos and BPE [Burk, M. J. et al, Organometallics 1990, 9, 2653; Burk, M. J. et al, *Angew. Chem., Int. Ed. Engl.* 1990, 29, 1462], Imamoto's BisP* [Imamoto, T. et al, J. Am. Chem. Soc. 1997, 119, 1799], Zhang's PennPhos [Zhang, X. et al, *Angew. Chem. Int. Ed. Engl.* 1999, 38, 516] and TangPhos [US2004/0229846 and Zhang, X. et al, *Angew. Chem. Int. Ed.* 2002, 41, 1613.], Pfizer's trichickenfootphos [WO2005/087370 and Hoge, G. et al, *J. Am. Chem. Soc.* 2004, 126, 5966].

Although tremendous progress has been made in the field of asymmetric hydrogenation and many efficient chiral ligands have been developed, the design of new efficient ligands continues to be important since there is no universal ligand for hydrogenation of various kinds of prochiral substrates.

BRIEF SUMMARY OF THE INVENTION

We have developed a series of novel and efficient chiral phosphorus ligands that have shown excellent reactivity and enantioselectivity in asymmetric hydrogenation. High enantioselectivity has been achieved in asymmetric hydrogenation of alpha-arylenamides, alpha-dehydroamino acid derivatives, and beta-dehydroamino acid derivatives.

BRIEF DESCRIPTION OF THE DRAWINGS

FIG. 1 shows an x-ray crystal structure of Rh[(nbd)((2R, 2'R,3R,3'R)—BIBOP)]BF$_4$ (the H atoms are omitted), where each of the letters on the atoms (C, O, P, Rh, B, and F) refer to carbon, oxygen, phosphorus, rhodium, boron and fluorine, respectively.

DETAILED DESCRIPTION OF THE INVENTION

Abbreviations

DCM=dichloromethane

DMF=dimethylformamide

EtOH=ethanol

EtOAC=ethyl acetate

MeOH=methanol

MTB=methyl tert-butyl ether nbd=norbornadiene

PCy=tri(cyclohexyl)phosphine

THF=tetrahydrofuran

TfO$^-$=trifluoromethanesulfonate or triflate

In its broadest embodiments, the present invention relates to novel phosphine ligands, novel metal complexes containing the novel phosphine ligands of the invention, and methods of using the novel metal complexes to carry out asymmetric hydrogenations as described below.

The Phosphine Ligands of the Invention

As noted above, in one embodiment, the present invention relates to a compound of formula (Ia), (Ib), or a mixture thereof ("the phosphine ligand of the invention"):

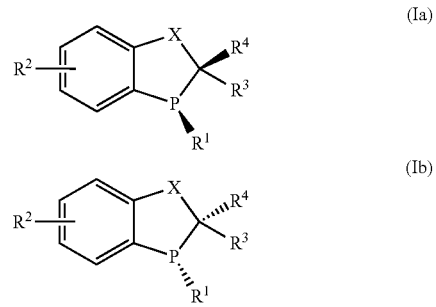

wherein:

X is O, S, or —NR$^5$;

R$^1$ is —(C$_1$-C$_6$)alkyl, —CF$_3$, —(C$_3$-C$_{10}$)carbocyclyl, -(5- to 11-membered)heterocarbocyclyl, —(C$_6$-C$_{10}$)aryl, -(5 to 11-membered)heteroaryl, or ferrocenyl; wherein said —(C$_3$-C$_{10}$)carbocyclyl, -(5- to 11-membered)heterocarbocyclyl, —(C$_6$-C$_{10}$)aryl and -(5 to 11-membered)heteroaryl of said R$^1$ is optionally substituted with 1 to 3 substituents independently selected from —O(C$_1$-C$_6$)alkyl, —(C$_1$-C$_6$)alkyl, and —CF$_3$;

R$^2$ is H, —O(C$_1$-C$_6$)alkyl, —(C$_1$-C$_6$)alkyl, —(C$_3$-C$_{10}$)carbocyclyl, -(5- to 11-membered)heterocarbocyclyl, —(C$_6$-C$_{10}$)aryl, -(5 to 11-membered)heteroaryl, —NR$^5$R$^6$, or —SR$^5$; wherein said —(C$_3$-C$_{10}$)carbocyclyl, -(5- to 11-membered)heterocarbocyclyl, —(C$_6$-C$_{10}$)aryl, and -(5 to 11-membered)heteroaryl of said R$^2$ is optionally substituted with 1 to 3 substituents independently selected from —O(C$_1$-C$_6$)alkyl, —(C$_1$-C$_6$)alkyl, and —CF$_3$;

R$^3$ is —PR$^7$R$^8$, —CH$_2$PR$^7$R$^8$, —CH$_2$OPR$^7$R$^8$, or a group of formula (A) or (B):

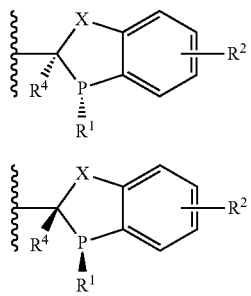

wherein X, $R^1$ and $R^2$ of the group of formula (A) or (B) are as defined above, and wherein the group of formula (A) only joins to the compound of formula (Ia), and the group of formula (B) only joins to the compound of formula (Ib);

$R^4$ is H, —($C_1$-$C_6$)alkyl, —($C_3$-$C_6$)cycloalkyl, -(3- to 6-membered)heterocycloalkyl, phenyl, (5- to 6-membered)heteroaryl, or —$SiR^5_3$; wherein said —($C_1$-$C_6$)alkyl of said $R^4$ is optionally substituted with 1 to 3 substituents independently selected from —O($C_1$-$C_6$)alkyl, —($C_3$-$C_6$)cycloalkyl, phenyl, and -(5- to 6-membered)heteroaryl; and wherein said —($C_3$-$C_6$)cycloalkyl, -(3- to 6-membered) heterocycloalkyl, phenyl, and (5- to 6-membered)heteroaryl of said $R^4$ is optionally substituted with 1 to 3 substituents independently selected from —O($C_1$-$C_6$)alkyl, —($C_1$-$C_6$)alkyl, and —$CF_3$;

$R^5$ and $R^6$ are each independently H, —($C_1$-$C_6$)alkyl, —$CF_3$, —($C_3$-$C_{10}$)carbocyclyl, -(5- to 11-membered)heterocarbocyclyl, —($C_6$-$C_{10}$)aryl, or -(5 to 11-membered)heteroaryl;

wherein each —($C_1$-$C_6$)alkyl, —$CF_3$, —($C_3$-$C_{10}$)carbocyclyl, -(5- to 11-membered)heterocarbocyclyl, —($C_6$-$C_{10}$) aryl, and -(5 to 11-membered)heteroaryl of said $R^5$ and $R^6$ is optionally independently substituted with 1 to 3 substituents independently selected from halo, —O($C_1$-$C_6$)alkyl, —($C_1$-$C_6$)alkyl, and —$CF_3$; and $R^7$ and $R^8$ are each independently —($C_1$-$C_6$)alkyl, —$CF_3$, —($C_3$-$C_{10}$)carbocyclyl, -(5- to 11-membered)heterocarbocyclyl, —($C_6$-$C_{10}$)aryl, -(5 to 11-membered)heteroaryl, or ferrocenyl; wherein said —($C_3$-$C_{10}$)carbocyclyl, -(5- to 11-membered)heterocarbocyclyl, —($C_6$-$C_{10}$)aryl and -(5 to 11-membered)heteroaryl of said $R^7$ and $R^8$ are each optionally independently substituted with 1 to 3 substituents independently selected from —O($C_1$-$C_6$)alkyl, —($C_1$-$C_6$)alkyl, and —$CF_3$.

In another embodiment, the invention relates to a compound of formula (Ia), (Ib), or a mixture thereof, according to the embodiment described immediately above, wherein X is O.

In another embodiment, the invention relates to a compound of formula (Ia), (Ib), or a mixture thereof, according to the broadest embodiment described above, wherein X is S.

In another embodiment, the invention relates to a compound of formula (Ia), (Ib), or a mixture thereof, according to the broadest embodiment described above, wherein X is $NR^5$.

In another embodiment, the invention relates to a compound of formula (Ia), (Ib), or a mixture thereof, according to any of the preceding embodiments, wherein $R^1$ is —($C_1$-$C_6$) alkyl selected from —$CH_3$, —$CH_2CH_3$, —$CH(CH_3)_2$, —$C(CH_3)_3$, —$C(CH_2CH_3)_3$, or —$C(CH_2CH_3)(CH_3)_2$.

In another embodiment, the invention relates to a compound of formula (Ia), (Ib), or a mixture thereof, according to the broadest embodiment described above, wherein $R^1$ is —($C_3$-$C_{10}$)carbocyclyl selected from cyclopentyl, cyclohexyl, and 1-adamantyl.

In another embodiment, the invention relates to a compound of formula (Ia), (Ib), or a mixture thereof, according to the broadest embodiment described above, wherein $R^1$ is —($C_6$-$C_{10}$)aryl selected from phenyl, ortho-tolyl, para-tolyl, 3,5-dimethylphenyl, 3,5-di-t-butylphenyl, 3,5-di-$CF_3$-phenyl, ortho-$CF_3$-phenyl, ortho-anisyl, and naphthyl.

In another embodiment, the invention relates to a compound of formula (Ia), (Ib), or a mixture thereof, according any of the preceding embodiments, wherein $R^2$ is H, —$CH_3$ or —$OCH_3$.

In another embodiment, the invention relates to a compound of formula (Ia), (Ib), or a mixture thereof, according to the broadest embodiment described above wherein $R^2$ is phenyl.

In another embodiment, the invention relates to a compound of formula (Ia), (Ib), or a mixture thereof, according any of the preceding embodiments, wherein $R^4$ is —H.

In another embodiment, the invention relates to a compound of formula (Ia), (Ib), or a mixture thereof, according to the broadest embodiment described above, wherein $R^4$ is —($C_1$-$C_6$)alkyl optionally substituted with 1 to 3 substituents independently selected from —$OCH_3$, —($C_3$-$C_6$)cycloalkyl, phenyl, and -(5- to 6-membered)heteroaryl.

In another embodiment, the invention relates to a compound of formula (Ia), (Ib), or a mixture thereof, according to the embodiment described immediately above, wherein $R^4$ is —$CH_2$(chiral oxazoline) or —$CH_2$(ortho-substituted pyridine).

In another embodiment, the invention relates to a compound of formula (Ia), (Ib), or a mixture thereof, according to the broadest embodiment described above, wherein $R^4$ is a -(5- to 6-membered)heteroaryl selected from ortho-substituted pyridine, oxazoline, and chiral oxazoline.

In another embodiment, the invention relates to a compound of formula (Ia), (Ib), or a mixture thereof, according to any of the preceding embodiments, wherein $R^3$ is —$PR^7R^8$ or a group of formula (A) ("the bis-phosphine ligand of the invention")

In another embodiment, the invention relates to a bis-phosphine ligand of the invention, wherein $R^1$ is —$C(CH_3)_3$; $R^2$ is —H, —$CH_3$, —$OCH_3$, or phenyl; and $R^3$ is —$PR^7R^8$.

In another embodiment, the invention relates to a bis-phosphine ligand of the invention, wherein $R^7$ and $R^8$ are each independently H, —($C_1$-$C_6$)alkyl, or —($C_3$-$C_6$)cycloalkyl.

In another embodiment, the invention relates to a bis-phosphine ligand of the invention, wherein $R^7$ and $R^8$ are each —$C(CH_3)_3$.

In another embodiment, the invention relates to a bis-phosphine ligand of the invention, wherein, X is S.

In another embodiment, the invention relates to a bis-phosphine ligand of the invention, wherein, X is O.

In another embodiment, the invention relates to a bis-phosphine ligand of the invention, wherein, X is $NR^5$.

In another embodiment the invention relates to a bis-phosphine ligand of the invention, wherein X is O, $R^1$ is —$C(CH_3)_3$; $R^2$ is —H, —$CH_3$, —$OCH_3$, or phenyl; and $R^3$ is —$PR^7R^8$.

In another embodiment, the invention relates to a bis-phosphine ligand of the invention, wherein $R^3$ is a group of formula (A) or (B).

In another embodiment, the invention relates to a bis-phosphine ligand of the invention, according to the embodiment described immediately above, wherein $R^1$ is —$C(CH_3)_3$; and $R^2$ is —H, —$CH_3$, —$OCH_3$, or phenyl.

In another embodiment, the invention relates to a bis-phosphine ligand of the invention, wherein X is O; $R^1$ is —C(CH$_3$)$_3$; and $R^2$ is —H, —CH$_3$, —OCH$_3$, or phenyl; and $R^3$ is a group of formula of formula (A) or (B).

In another embodiment, the invention relates to a bis-phosphine ligand of the invention having the formula (IIa) or (IIb)

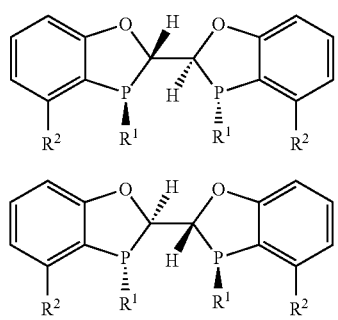

(IIa)

(IIb)

wherein:
$R^1$ is —CH(CH$_3$)$_2$, —C(CH$_3$)$_3$, —C(CH$_2$CH$_3$)(CH$_3$)$_2$, cyclohexyl, 1-adamantyl, phenyl, ortho-tolyl, 3,5-xylyl, ortho-anisyl, or ferrocenyl; and
$R^2$ is H, —OCH$_3$, —CH$_3$, —CF$_3$, phenyl, or —N(CH$_3$)$_2$.

In another embodiment, the invention relates to a bis-phosphine ligand of the invention having the formula (IIIa) or (IIIb):

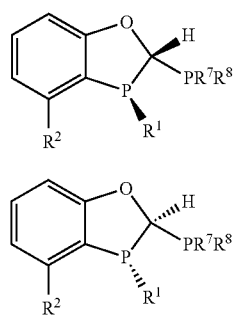

(IIIa)

(IIIb)

wherein
$R^1$ is —CH(CH$_3$)$_2$, —C(CH$_3$)$_3$, —C(CH$_2$CH$_3$)(CH$_3$)$_2$, cyclohexyl, or 1-adamantyl;
$R^2$ is H, —OCH$_3$, —CH$_3$, —CF$_3$, phenyl, or —N(CH$_3$)$_2$; and
$R^7$ and $R^8$ are each —C(CH$_3$)$_3$.

In one embodiment, the invention relates to a phosphine ligand of the invention selected from:
(2S,2'S,3S,3'S)-3,3'-di-tert-butyl-2,2',3,3'-tetrahydro-2,2'-bibenzo[d][1,3]oxaphosphole,
(2S,2'S,3S,3'S)-3,3'-di-tert-butyl-4,4'-dimethoxy-2,2',3,3'-tetrahydro-2,2'-bibenzo[d][1,3]oxaphosphole,
(2S,2'S,3S,3'S)-3,3'-di-tert-butyl-4,4'-diphenyl-2,2',3,3'-tetrahydro-2,2'-bibenzo[d][1,3]oxaphosphole,
(2S,2'S,3S,3'S)-3,3'-di-tert-butyl-4,4'-dimethyl-2,2',3,3'-tetrahydro-2,2'-bibenzo[d][1,3]oxaphosphole,
(2S,3R)-3-tert-butyl-2-(di-tert-butylphosphino-4-methoxy)-2,3-dihydrobenzo[d][1,3]oxaphosphole, and
(2S,3R)-3-tert-butyl-2-(di-tert-butylphosphino)-2,3-dihydrobenzo[d][1,3]oxaphosphole.

The Metal Complexes of the Invention

As noted above, the invention relates to complexes formed between a transition metal and the phosphine ligands of the invention. Accordingly, in one embodiment, the invention relates to a metal complex of formula (IVa), (IVb), (Va) or (Vb) ("the metal complexes of the invention"):

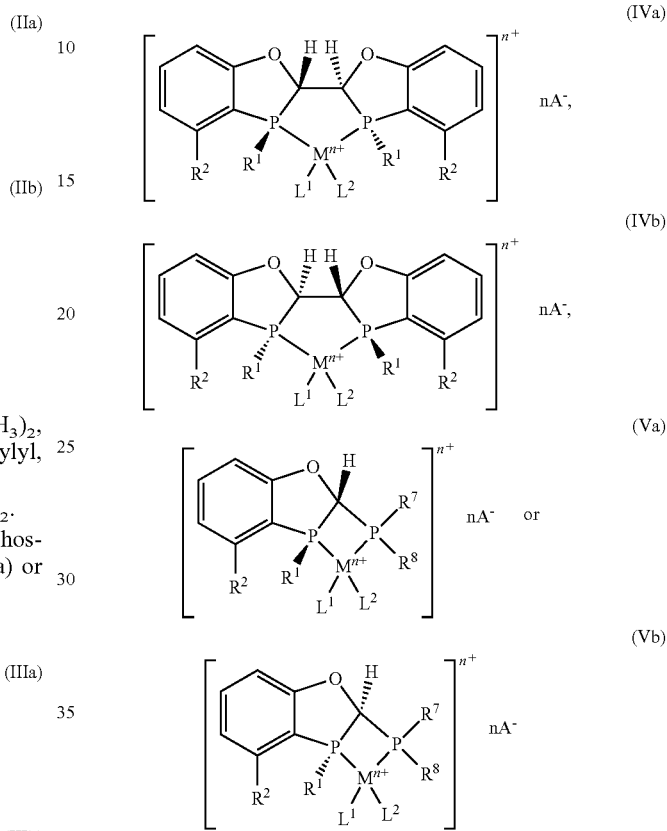

(IVa)

(IVb)

(Va)

(Vb)

wherein
M is a transition metal selected from Co, Ni, Pd, Pt, Cu, Ag, Au, Ru, Fe, Rh and Ir;
A$^-$ is a counter anion;
n is the oxidation state of the transition metal M;
$L^1$ and $L^2$ are each olefins, or $L^1$ and $L^2$ together represent a diolefin;
X is O, S, or —NR$^5$;
$R^1$ is —(C$_1$-C$_6$)alkyl, —CF$_3$, —(C$_3$-C$_{10}$)carbocyclyl, -(5- to 11-membered)heterocarbocyclyl, —(C$_6$-C$_{10}$)aryl, -(5 to 11-membered)heteroaryl, or ferrocenyl; wherein said —(C$_3$-C$_{10}$)carbocyclyl, -(5- to 11-membered)heterocarbocyclyl, —(C$_6$-C$_{10}$)aryl and -(5 to 11-membered)heteroaryl of said $R^1$ is optionally substituted with 1 to 3 substituents independently selected from —O(C$_1$-C$_6$) alkyl, —(C$_1$-C$_6$)alkyl, and —CF$_3$;
$R^2$ is H, —O(C$_1$-C$_6$)alkyl, —(C$_1$-C$_6$)alkyl, —(C$_3$-C$_{10}$)carbocyclyl, -(5- to 11-membered)heterocarbocyclyl, —(C$_6$-C$_{10}$)aryl, -(5 to 11-membered)heteroaryl, —NR$^5$R$^6$, or —SR$^5$; wherein said —(C$_3$-C$_{10}$)carbocyclyl, -(5- to 11-membered)heterocarbocyclyl, —(C$_6$-C$_{10}$)aryl, and -(5 to 11-membered)heteroaryl of said $R^2$ is optionally substituted with 1 to 3 substituents independently selected from —O(C$_1$-C$_6$)alkyl, —(C$_1$-C$_6$)alkyl, and —CF$_3$;
$R^5$ and $R^6$ are each independently H, —(C$_1$-C$_6$)alkyl, —CF$_3$, —(C$_3$-C$_{10}$)carbocyclyl, -(5- to 11-membered)heterocarbocyclyl, —(C$_6$-C$_{10}$)aryl, or -(5 to 11-membered)heteroaryl; wherein each —($C_1$-$C_6$)alkyl, —$CF_3$, —($C_3$-$C_{10}$) carbocyclyl, -(5- to 11-membered)heterocarbocyclyl, —($C_6$-$C_{10}$)aryl, and -(5 to 11-membered)heteroaryl of said $R^5$ and $R^6$ is optionally independently substituted with 1 to 3 substituents independently selected from halo, —O($C_1$-$C_6$)alkyl, —($C_1$-$C_6$)alkyl, and —$CF_3$; and $R^7$ and $R^8$ are each independently —($C_1$-$C_6$)alkyl, —$CF_3$, —($C_3$-$C_{10}$)carbocyclyl, -(5- to 11-membered)heterocarbocyclyl, —($C_6$-$C_{10}$)aryl, -(5 to 11-membered)heteroaryl, or ferrocenyl; wherein said —($C_3$-$C_{10}$)carbocyclyl, -(5- to 11-membered)heterocarbocyclyl, —($C_6$-$C_{10}$)aryl and -(5 to 11-membered)heteroaryl of said $R^7$ and $R^8$ are each optionally independently substituted with 1 to 3 substituents independently selected from —O($C_1$-$C_6$)alkyl, —($C_1$-$C_6$)alkyl, and —$CF_3$.

In another embodiment, the invention relates to a metal complex of the invention wherein M is Rh and n is 1.

In another embodiment, the invention relates to a metal complex of the invention according to any of the two embodiments described immediately above, wherein $A^-$ is $BF_4^-$, $SbF_6^-$, $TfO^-$, $B(C_6H_5)_4^-$, $B[3,5-(CF_3)_2C_6H_3]_4^-$, or $PF_6^-$.

In another embodiment, the invention relates to a metal complex of the invention according to any of the three embodiments described immediately above, wherein M is Rh, $A^-$ is $BF_4^-$, and n is 1.

In another embodiment, the invention relates to a metal complex of the invention according to any of the four embodiments described immediately above, wherein $R^1$ is —$C(CH_3)_3$, and $R^2$ is —H, —$CH_3$, —$OCH_3$, or phenyl.

In another embodiment, the invention relates to a metal complex of the invention wherein $L^1$ and $L^2$ together represent a diolefin selected from norbornadiene and cyclooctadiene.

In another embodiment, the invention relates to a metal complex of the invention, wherein the metal complex is of formula (IVa).

In another embodiment, the invention relates to a metal complex of the invention according to the embodiment immediately above, wherein M is Rh, $A^-$ is $BF_4^-$; and n is 1.

In another embodiment, the invention relates to a metal complex of the invention according to the embodiment immediately above, wherein $L^1$ and $L^2$ together represent a diolefin selected from norbornadiene and cyclooctadiene.

In another embodiment, the invention relates to a metal complex of the invention, wherein the metal complex is of formula (Va).

In another embodiment, the invention relates to a metal complex of the invention according to the embodiment immediately above, wherein M is Rh, $A^-$ is $BF_4^-$; and n is 1.

In another embodiment, the invention relates to a metal complex of the invention according to the embodiment immediately above, wherein $L^1$ and $L^2$ together represent a diolefin selected from norbornadiene and cyclooctadiene.

In another embodiment, the invention relates to a metal complex of the invention, wherein the metal complex is of formula (IVb).

In another embodiment, the invention relates to a metal complex of the invention according to the embodiment immediately above, wherein M is Rh, $A^-$ is $BF_4^-$; and n is 1.

In another embodiment, the invention relates to a metal complex of the invention according to the embodiment immediately above, wherein $L^1$ and $L^2$ together represent a diolefin selected from norbornadiene and cyclooctadiene.

In another embodiment, the invention relates to a metal of the invention, wherein the metal complex is of formula (Vb).

In another embodiment, the invention relates to a metal complex of the invention according to the embodiment immediately above, wherein M is Rh, $A^-$ is $BF_4^-$; and n is 1.

In another embodiment, the invention relates to a metal complex of the invention according to the embodiment immediately above, wherein $L^1$ and $L^2$ together represent a diolefin selected from norbornadiene and cyclooctadiene.

In one embodiment, the invention relates to a metal complex of the invention selected from:

Rh[(2S,2'S,3S,3'S)-3,3'-di-tert-butyl-2,2',3,3'-tetrahydro-2,2'-bibenzo[d][1,3]oxaphosphole(nbd)]$BF_4$, Rh[(2S,2'S,3S,3'S)-3,3'-di-tert-butyl-4,4'-dimethoxy-2,2',3,3'-tetrahydro-2,2'-bibenzo[d][1,3]oxaphosphole(nbd)]$BF_4$, Rh[(2S,2'S,3S,3'S)-3,3'-di-tert-butyl-4,4'-diphenyl-2,2',3,3'-tetrahydro-2,2'-bibenzo[d][1,3]oxaphosphole(nbd)]$BF_4$, Rh[(2S,2'S,3S,3'S)-3,3'-di-tert-butyl-4,4'-dimethyl-2,2',3,3'-tetrahydro-2,2'-bibenzo[d][1,3]oxaphosphole(nbd)]$BF_4$, Rh[(2S,3R)-3-tert-butyl-2-(di-tert-butylphosphino)-4-methoxy-2,3-dihydrobenzo[d][1,3]oxaphosphole(nbd)]$BF_4$ and Rh[(2S,3R)-3-tert-butyl-2-(di-tert-butylphosphino)-2,3-dihydrobenzo[d][1,3]-oxaphosphole(nbd)]$BF_4$.

Asymmetric Hydrogenation

In one embodiment, the invention relates to a process for the asymmetric hydrogenation of a compound having a carbon-carbon or carbon-heteroatom double bond ("the asymmetric hydrogenation process of the invention"), the process comprising allowing said compound having a carbon-carbon or carbon-heteroatom double bond to react with hydrogen in the presence of a catalytic amount of the metal complex of the invention described in any of the embodiments above. Non-limiting examples of carbon-heteroatom double bonds include those formed between carbon and nitrogen, oxygen, or sulfur. In a preferred embodiment, carbon-heteroatom double bond is formed between carbon and nitrogen or carbon and oxygen.

In another embodiment, the invention relates to the asymmetric hydrogenation process of the invention in the embodiment described immediately above, wherein $L^1$ and $L^2$ together represent norbornadiene.

In another embodiment, the invention relates to the asymmetric hydrogenation process of the invention in the broadest embodiment described above, wherein $L^1$ and $L^2$ together represent octadiene.

In another embodiment, the invention relates to the asymmetric hydrogenation process of the invention in any of the embodiments described above, wherein M is Rh, $A^-$ is $BF_4^-$, and n is 1.

In another embodiment, the invention relates to the asymmetric hydrogenation process of the invention in any of the embodiments described above, wherein $R^1$ is —$C(CH_3)_3$; $R^2$ is —H, —$CH_3$, —$OCH_3$, or phenyl; and $R^7$ and $R^8$ are each —$C(CH_3)_3$.

Unless stated otherwise, the term "compounds of the invention" refers to the phosphine ligands of the invention (including bis-phosphine ligands of the invention) and the metal complexes of the invention.

For all compounds of the invention disclosed hereinabove in this application, in the event the nomenclature is in conflict with the structure, it shall be understood that the compound is defined by the structure.

Compounds of the invention also include their isotopically-labelled forms. An isotopically-labelled form of a compound of the present invention is identical to said compound of the invention but for the fact that one or more atoms of said compound of the invention have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. A compound of the present invention which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" or "$O(C_{1-6})$ alkyl" is a $(C_{1-6})$alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$(C_{3-10})$carbocycle" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$(C_{6-10})$aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "(5 to 11-membered)heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "(5 to 11-membered)heteroaryl" refers to an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

It will be understood that one to three carbon ring moieties in the each of the ($C_{3-10}$) carbocyclic rings, the (5 to 11-membered)heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above.

The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The term "olefin" as used herein refers to an unsaturated hydrocarbon containing carbon atoms linked by a double bond (i.e., an alkene) such as, for example, ethylene, propene, 1-butene, 2-butene, styrene, norbornadiene, or cyclooctadiene. The term "diolefin" refers an unsaturated hydrocarbon containing two pairs of carbon atoms linked by double bonds, e.g., norbornadiene, or cyclooctadiene.

The compounds of the invention may be made using the general synthetic methods described below, which also constitute part of the invention.

General Synthetic Methods

The invention also provides processes for making compounds of formula Ia, Ib, IIa, IIb, IIIa, IIIb, IVa, IVb, Va and Vb. In all methods, unless specified otherwise, $R^1$, $R^2$, $R^3$, $R^4$, $R^7$, $R^8$, $L^1$, $L^2$, A, M and n in the formulas below shall have the meaning of $R^1$, $R^2$, $R^3$, $R^4$, $R^7$, $R^8$, $L^1$, $L^2$, A, M and n in formula Ia, Ib, IIa, IIb, IIIa, IIIb, IVa, IVb, Va and Vb of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Examples section. Typically, reaction progress may be monitored by thin layer chromatography (TLC), if desired, and intermediates and products may be purified by chromatography on silica gel and/or by recrystallization. The examples which follow are illustrative and, as recognized by one skilled in the art, particular reagents or conditions could be modified as needed for individual compounds without undue experimentation.

Starting materials and reagents are either commercially available or may be prepared by one skilled in the art using methods described in the chemical literature. Initial products of formula Ia, Ib, IIa, IIb, IIIa, IIIb, IVa, IVb, Va and Vb may be modified further by methods known in the art to produce additional compounds of formula Ia, Ib, IIa, IIb, IIIa, IIIb, IVa, IVb, Va and Vb.

Compounds of formula Ia, Ib, IIa and IIb wherein X is O, may be prepared as shown in Scheme 1.

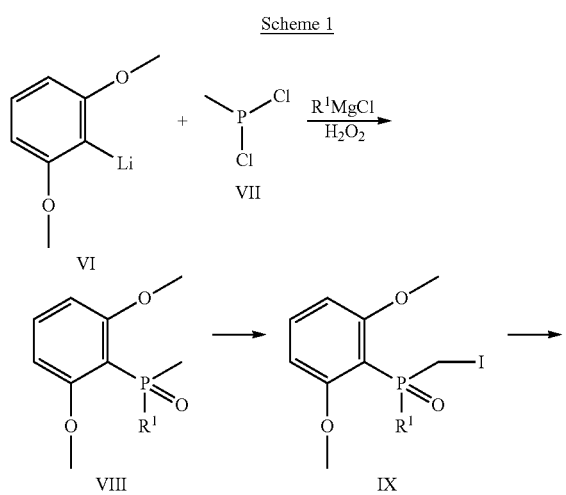

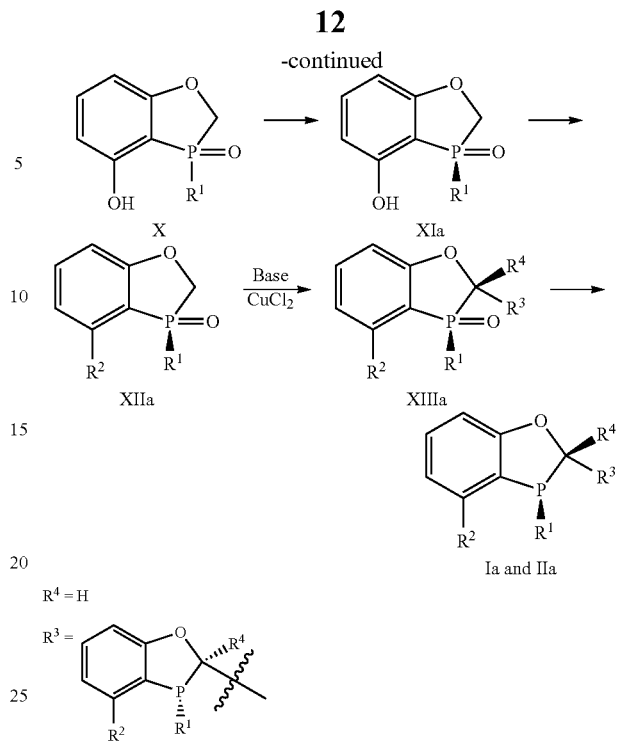

As illustrated in Scheme 1, reaction of dimethoxy phenyl-lithium VI with a dichlorophosphine of formula VII, in a suitable solvent, in the presence of an alkyl magnesium chloride and hydrogen peroxide provides a phosphine oxide of formula VIII. Iodination of the phosphine oxide VIII, in a suitable solvent, in the presence of a suitable base, provides the iodinated intermediate of formula IX. Demethylation of the methoxy groups of compound IX by a reagent such as boron tribromide ($BBr_3$) followed by cyclization, provides the corresponding cyclized intermediate of formula X. Resolution of the intermediate X using a resolving agent such as (+) menthyl chloroformate provides the corresponding (R) isomer of formula XIa. The hydroxyl group of compound XIa may be modified to other groups, such as methoxy, aryl etc., under standard reaction conditions known in the literature, to provide a compound of formula XIIa. Reaction of the compound of formula XIIa, in a suitable solvent, in the presence of suitable base and copper chloride provides the corresponding bisphosphine oxide of formula XIIIa. Reduction of the bisphosphine oxide XIIIa provides a compound of formula Ia or IIa. Alternately, resolution of the intermediate X using a resolving agent such as (−) menthyl chloroformate provides the corresponding (S) isomer XIb which may be converted to compounds of formula Ib or IIb using the above Scheme.

Compounds of formula IIIa and IIIb may be prepared as illustrated in Scheme 2.

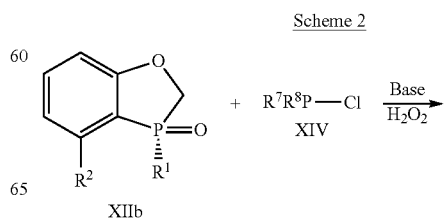

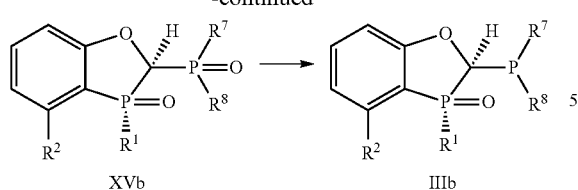

XVb → IIIb

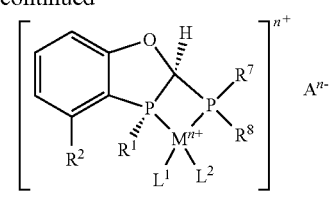

Vb

As illustrated in Scheme 2, reaction of a compound of formula XIIb, obtained via Scheme 1, with a phosphorus chloride of formula XIV, in the presence of a suitable base and hydrogen peroxide, provides a bisphosphine oxide of formula XVb. Reduction of the bisphosphine oxide XVb as in Scheme 1, provides a compound of formula IIIb. Alternately, A compound of formula XIIa may be converted to a compound of formula IIIa using the method depicted in Scheme 2.

Compounds of formula IVa and IVb may be prepared according to Scheme 3

As illustrated in Scheme 4, reaction of a compound of formula IIIb with a transition metal salt [M(L¹L²)]$^{n+}$ nA$^-$, in a suitable solvent, provides a compound of formula Vb. Similarly, starting with a compound of formula IIIa provides the corresponding compound of formula Va.

Compounds of formula Ia and Ib may also be prepared as shown in Scheme 5.

Scheme 3

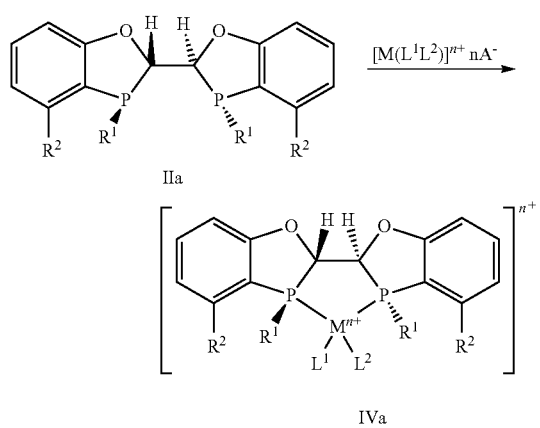

IIa

IVa

Scheme 5

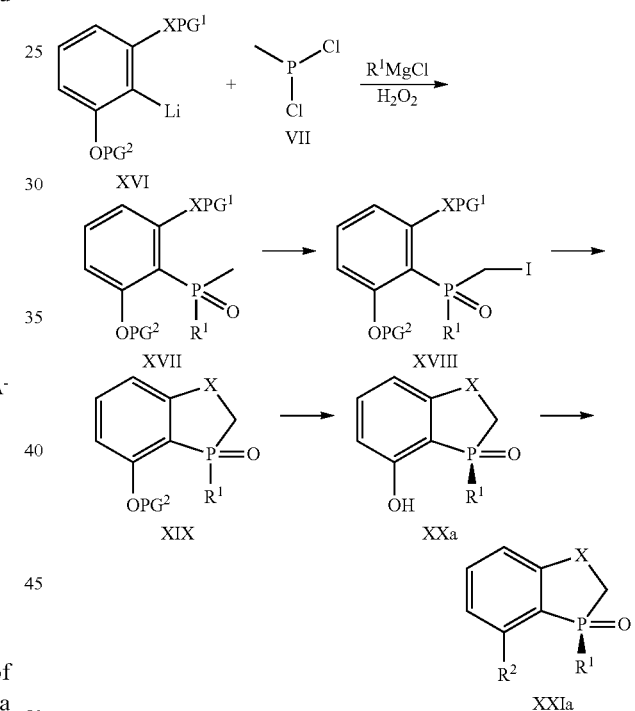

As illustrated in Scheme 3, reaction of a compound of formula IIa with a transition metal salt [M(L¹L²)]$^{n+}$ nA$^-$, in a suitable solvent, provides a compound of formula IVa. Similarly, starting with a compound of formula IIb provides the corresponding compound of formula IVb.

Compounds of formula Va and Vb may be prepared according to Scheme 4

Scheme 4

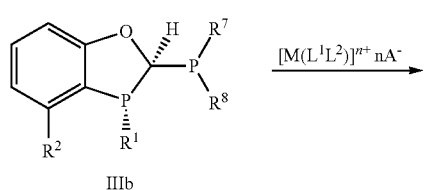

IIIb

As illustrated in Scheme 5, reaction of a compound of formula XVI with a dichlorophosphine of formula VII, in a suitable solvent, in the presence of an alkyl magnesium chloride and hydrogen peroxide provides a phosphine oxide of formula XVII. X=O, S or NR$^5$, PG$^1$ and PG$^2$ are suitable protecting groups such as methyl, benzyl, methoxymethyl etc. Iodination of the phosphine oxide XVII, in a suitable solvent, in the presence of a suitable base, provides the iodinated intermediate of formula XVIII. Deprotection of compound XVIII followed by cyclization, provides the corresponding cyclized intermediate of formula XIX. Further deprotection of compound XIX followed by the resolution of the intermediate hydroxyl compound using a resolving agent such as (+) menthyl chloroformate, provides the corresponding (R) isomer of formula XXa. The hydroxyl group of compound XXa may be modified to other groups, such as methoxy, aryl etc., under standard reaction conditions known in the literature to provide a compound of formula XXIa. Compound XXIa may be converted to a compound of formula Ia by the method shown in Scheme 1.

Alternately, resolution of the intermediate using a resolving agent such as (−) menthyl chloroformate provides the corresponding (S) isomer XXIb which may be converted to compounds of formula Ib by the method described in Scheme 1.

All of the compounds of the invention may prepared by the methods described above and in the Examples section below.

EXAMPLES

Examples 1-4

Examples 1-4 describe the preparation of (R)-3-tert-butyl-2,3-dihydrobenzo[d][1,3]oxaphosphol-4-ol oxide ((R)-3) as depicted below:

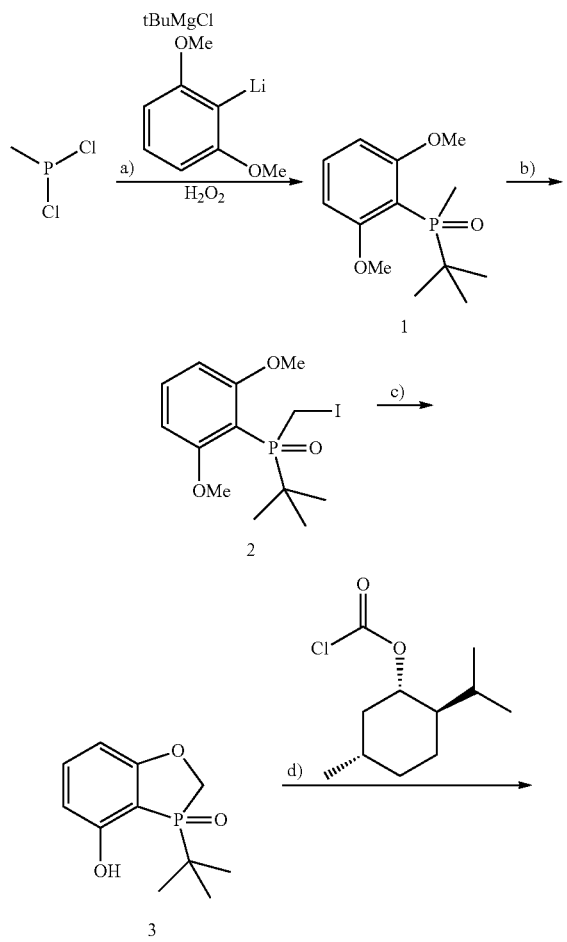

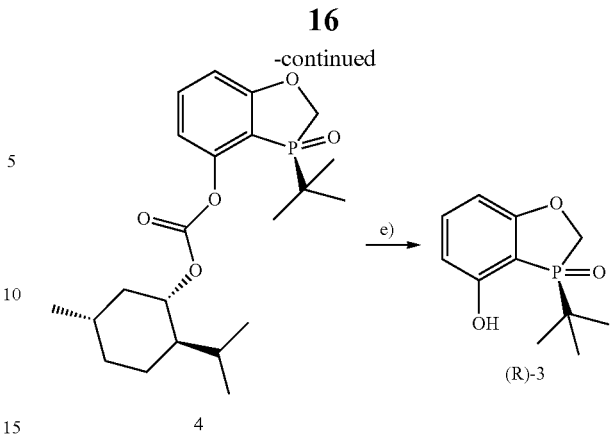

Example 1 Preparation of tert-butyl(2,6-dimethoxyphenyl)(methyl)phosphine oxide (1). To a solution of dichloromethylphosphine (6.61 g, 57 mmol, 1.0 equiv.) in THF (50 mL) was added dropwise 1.0 M tBuMgCl (57 mL, 57 mmol, 1.0 equiv.) over 1 h while controlling the reaction temperature <−10° C. The mixture was stirred at −10 to 0° C. for 1 h and then warmed to 25° C. over 1 h and stirred at 25° C. for at least 1 h. To a solution of 1,3-dimethoxybenzene (9.37 g, 68 mmol, 1.2 equiv.) in THF (50 mL) in a separated flask was added 1.6 M BuLi (42.4 mL, 68 mmol, 1.2 equiv.) over 1 h while controlling the temperature <0° C. The mixture was further stirred at 0° C. for 0.5 h. To the aforementioned mixture of dichloromethylphosphine and $^t$BuMgCl was added dropwise the mixture of in situ generated 2,6-dimethoxyphenyllithium made above over 0.5 h while controlling the reaction temperature <25° C. The resulting mixture was further stirred at 25° C. for 1 h. To the mixture was added dropwise 30% $H_2O_2$ over 10 min at 0° C. and the mixture was further stirred at 25° C. for 0.5 h, and then quenched with addition of 2 N HCl (300 mL) and dichloromethane (300 mL). The dichloromethane layer was washed with brine (300 mL), dried over magnesium sulfate, and purified by column chromatography (eluents: EtOAc to EtOAc/MeOH 4/1; monitored at 290 nm) to provide 1 as a thick oil (9.5 g, 37 mmol, 65%). 1: $^1$HNMR (400 MHz, $CDCl_3$): δ=7.41 (m, 1H), 6.60 (dd, J=8.4, 3.8 Hz, 2H), 3.84 (s, 6H), 1.83 (d, J=13.2 Hz, 3H), 1.18 (d, J=15.4 Hz, 9H); $^{31}$PNMR (162 MHz, $CDCl_3$): δ=51.4; $^{13}$CNMR (100 MHz, $CDCl_3$): δ=163.1 (d, J=1.0 Hz), 133.7 (d, J=1.0 Hz), 107.3 (d, J=82 Hz), 104.5 (d, J=6 Hz), 55.65, 34.6 (d, J=72 Hz), 24.4 (d, J=1.6 Hz), 15.8 (d, J=69 Hz); ESI-MS: m/z 257 [M+H]$^+$.

Example 2: Preparation of tert-butyl(2,6-dimethoxyphenyl)(iodomethyl)phosphine (2). To a solution of 1 (7.4 g, 28.9 mmol, 1 equiv.) and TMEDA (6.50 mL, 43 mmol, 1.5 equiv.) in THF (40 mL) at −78° C. was added 2.5 M BuLi in hexanes (13.9 mL, 35 mmol, 1.2 equiv.) over 10 min. The resulting mixture was stirred at −78° C. for 1 h. To the mixture at −78° C. was added iodine (11.0 g, 43 mmol, 1.5 equiv.) in THF (20 mL) while controlling the temperature <−70° C. After the addition, the mixture was further stirred at −78° C. for 0.5 h and then warmed to 25° C. over 1 h. To the mixture was added 10% $NaHSO_3$ solution (100 mL) and dichloromethane (100 mL). The dichloromethane layer was washed with brine (100 mL), dried over sodium sulfate, concentrated, and purified by silica gel column chromatography (eluents: EtOAc to EtOAc/MeOH 10/1; monitored at 290 nm) to provide 2 as a thick oil (8.8 g, 23.0 mmol, 80%). $^1$HNMR (400 MHz, $CDCl_3$): δ=7.40 (t, J=8.4 Hz, 1H), 6.56 (dd, J=8.4, 4.0 Hz, 2H), 3.80 (s, 6H), 3.79 (m, 1H), 3.34 (dd, J=11.2, 8.3 Hz, 1H), 1.18 (d, J=15.6 Hz, 9H); $^{31}$PNMR (162 MHz, $CDCl_3$): δ=50.4; $^{13}$CNMR (100 MHz, $CDCl_3$): δ=163.2, 134.2, 104.9 (d, J=63

Hz), 104.3 (d, J=6 Hz), 55.9, 35.3 (d, J=71 Hz), 25.0, −1.8 (d, J=59 Hz); ESI-MS: m/z 383 [M+H]$^+$.

Example 3: Preparation of racemic 3-tert-butyl-2,3-dihydrobenzo[d][1,3]oxaphosphol oxide-4-ol (3). To a mixture of 2 (8.1 g, 21.2 mmol) in 1,2-dichloroethane (100 mL) at 0° C. was added BBr$_3$ (21.2 g, 64.8 mmol, 4 equiv.). The mixture was warmed to 60° C. over 0.5 h and stirred at ~60° C. for 2 h. To the mixture was carefully added MeOH (200 mL) while cooling and then concentrated. MeOH (200 mL×3) was further added and evaporated for three times to provide a residue as thick oil. To the residue was further added K$_2$CO$_3$ (14.6 g, 105 mmol, 5 equiv.) and DMF (100 mL). The mixture was stirred at 60° C. for 2 h and then cooled to 0° C. Water (200 mL) was added followed by conc. HCl to adjust the pH of the mixture to ~3. To the mixture was added dichloromethane (200 mL). The dichloromethane layer was separated and the aqueous layer was further washed twice with dichloromethane (50 mL×2). The combined dichloromethane layer was washed with brine (100 mL), dried over sodium sulfate, and purified by column chromatography (eluent: EtOAc/MeOH 4:1, monitored at 290 nm) to provide 3 as a white solid (4.3 g, 19.1 mmol, 90% yield). $^1$HNMR (400 MHz, CD$_3$OD): δ=7.33 (t, J=8.2 Hz, 1H), 6.45 (m, 2H), 4.72 (dd, J=14.3, 3.3 Hz, 1H), 4.30 (dd, J=14.3, 10.7 Hz, 1H), 1.28 (d, J=16.6 Hz, 9H); $^{31}$PNMR (162 MHz, CDCl$_3$): δ=68.6; $^{13}$CNMR (100 MHz, CD$_3$OD): δ=168.5 (d, J=17.2 Hz), 161.4 (d, J=2.2 Hz), 138.3, 109.0 (d, J=6.1 Hz), 105.5 (d, J=5.4 Hz), 101.7 (d, J=94.3 Hz), 67.0 (d, J=61 Hz), 34.5 (d, J=74 Hz), 24.9; ESI-MS: m/z 227 [M+H]$^+$.

Example 4: Preparation of (R)-3-tert-butyl-2,3-dihydrobenzo[d][1,3]oxaphosphol-4-ol oxide ((R)-3). To a mixture of racemic 3 (3.1 g, 13.7 mmol) and triethylamine (2.77 g, 27.4 mmol, 2 equiv) in methylene chloride (40 mL) was added (+)-menthyl chloroformate (3.6 g, 16.4 mmol, 1.2 equiv) at 0° C. over 5 min. The mixture was allowed to warm to 25° C. over 0.5 h and stirred at 25° C. for 2 h, then quenched by addition of water (100 mL). The methylene chloride layer was washed with brine, dried over Na$_2$SO$_4$, and purified by column chromatography (eluent: hexane/EtOAc to EtOAc, monitored at ~290 nm) to give a mixture of (+)-menthyl carbonate diastereomers (5.6 g, 13.7 mmol, 100%). The mixture was further treated with benzene (15 mL) and heated to reflux to form a clean solution. Crystallization by cooling down to 25° C. and filtration provided optically pure diastereomer in 42% yield (>99% de). $^1$HNMR (400 MHz, CDCl$_3$): δ=7.46 (t, J=8.2 Hz, 1H), 7.01 (m, 1H), 6.79 (m, 1H), 4.57 (m, 2H), 4.42 (dd, J=13.9, 10.7 Hz, 1H), 2.20 (m, 1H), 1.98 (m, 1H), 1.69 (m, 2H), 1.49 (m, 2H), 1.23 (dd, J=16.4, 1.9 Hz, 9H), 1.95-1.21 (m, 2H), 0.90 (td, J=8.9, 1.9 Hz, 6H), 0.86 (m, 1H), 0.78 (d, J=6.9 Hz, 3H); $^{13}$PNMR (162 MHz, CDCl$_3$): δ=62.78; $^{13}$CNMR (100 MHz, CDCl$_3$): δ=166.0 (d, J=16 Hz), 152.2 (d, J=23 Hz), 135.9, 114.5 (d, J=5 Hz), 111.0 (d, J=5 Hz), 106.8 (d, J=88 Hz), 80.1, 66.1 (d, J=60 Hz), 46.8, 40.3, 34.0, 33.7 (d, J=73 Hz), 31.4, 25.9, 24.2, 23.1, 21.9, 20.7, 16.0; ESI-MS: m/z 409 [M+H]$^+$. Note: Chiral HPLC conditions for separation of diastereomers: Chiralcel OD-H, n-heptane/isopropanol 95/5, 25° C.

To a solution of the aforementioned solid (0.4 g, 0.98 mmol) in EtOH (8 mL) was added at 25° C. a solution of KOH (0.411 g, 7.34 mmol, 20 equiv.) in water (2 mL). The mixture was stirred at 25° C. for 2 h. LC showed complete conversion of SM. To the mixture at 0° C. was added conc. HCl to control the pH ~4 followed by dichloromethane (20 mL). The dichloromethane layer was washed with brine, dried over sodium sulfate, and purified by column chromatography (silica gel, eluent: EtOAc/MeOH 4:1, monitored at ~290 nm) to provide ((R)-3) as white solid (200 mg, 0.88 mmol, 90% yield). Chiral separation: chrialpak AD-H, heptane/isopropanol (95:5), 2 ml/min, isocratic, 9.60 min (enantiomer), 16.60 min (this configuration).

Examples 5-8

Examples 5-8 describe the preparation of preparation of Preparation of Rh[(2S,2'S,3S,3'S)—BIBOP(nbd)]BF$_4$ (9a) as depicted below:

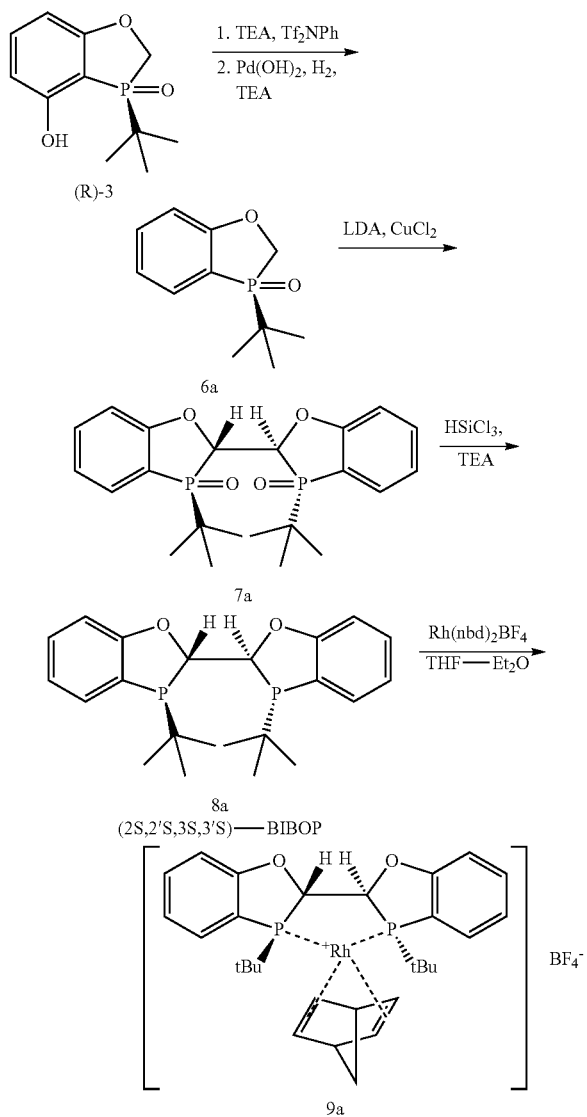

Example 5: Preparation of (R)-3-tert-butyl-2,3-dihydrobenzo[d][1,3]oxaphosphole (6a). To a solution of (R)-3, 50 mg, 0.221 mmol) and triethylamine (89 mg, 0.88 mmol, 4 equiv) in CH$_2$Cl$_2$ (2 mL) at 0° C. was added Tf$_2$NPh (96 mg, 0.27 mmol, 1.2 equiv) over 1 min. The mixture was stirred at 25° C. for 2 h and then quenched with addition of water (2 mL). The CH$_2$Cl$_2$ layer was separated, dried over sodium sulfate, concentrated, and purified by silica gel column chromatography (eluents: hexanes to EtOAc) to provide the triflate product (65 mg, 0.18 mmol, 82%) as white solid. $^1$HNMR (500 MHz, CD$_2$Cl$_2$): δ=7.58 (t, J=8.3 Hz, 1H), 7.03 (dd, J=8.2, 3.5 Hz, 1H), 7.00 (dd, J=8.5, 2.4 Hz, 1H), 4.67 (dd, J=14.2, 2.1 Hz, 1H), 4.46 (dd, J=14.1, 11.1 Hz, 1H), 1.21 (d, J=16.8 Hz, 9H); $^{31}$PNMR (202 MHz, CD$_2$Cl$_2$): δ=75.6; $^{13}$CNMR (125 MHz, CD$_2$Cl$_2$): δ=167.1 (d, J=16.8 Hz), 150.0, 137.1, 120.3, 117.8, 114.7 (d, J=4.4 Hz), 114.2 (d, J=4.3 Hz), 66.9 (d, J=59.3 Hz), 34.7 (d, J=72.0 Hz), 24.2; ESI-MS: m/z 359 [M+H]$^+$.

To a solution of the triflate (300 mg, 0.836 mmol, 1.0 equiv) in EtOAc (4 mL) was added triethylamine (1 mL) and 20% Pd(OH)$_2$/C (100 mg, wet). The mixture was stirred at 25° C. under 100 psi H$_2$ for 12 h, then filtered over Celite, and concentrated. The residue was re-dissolved in dichloromethane (4 mL), washed with water (5 mL), concentrated, and purified by silica gel column chromatography (eluent: EtOAc to EtOAc/MeOH 2:1) to provide 6a (155 mg, 0.737 mmol, 88%) as a white solid. $^1$HNMR (400 MHz, CDCl$_3$): δ=7.62 (m, 1H), 7.47 (m, 1H), 7.06 (m, 1H), 6.96 (m, 1H), 4.57 (m, 1H), 4.40 (m, 1H), 1.21 (dd, J=16.0, 3.8 Hz, 9H); $^{31}$PNMR (162 MHz, CDCl$_3$): δ=63.2; $^{13}$CNMR (100 MHz, CDCl$_3$): δ=165.0, 134.9 (d, J=1.7 Hz), 129.3 (d, J=6.5 Hz), 122.0 (d, J=9.2 Hz), 113.9 (d, J=5.5 Hz), 112.9, 65.0 (d, J=59.0 Hz), 33.2 (d, J=71.3 Hz), 23.6; ESI-MS: m/z 211 [M+H]$^+$.

Example 6: Preparation of (2S,2'S,3R,3'R)-3,3'-di-tert-butyl-2,2',3,3'-tetrahydro-2,2'-bibenzo[d][1,3]oxaphosphole bisoxide (7a). To a solution of 6a (155 mg, 0.737 mmol, 1 equiv) in THF (4 mL) at −78° C. was added LDA (0.49 mL, 1.8 M in heptane/THF/chlorobenzene, 0.884 mmol, 1.2 equiv). The mixture was stirred at −78° C. for 1 h before addition of anhydrous CuCl$_2$ (0.299 g, 2.21 mmol, 3 equiv) in one portion. The resulting mixture was kept at −78° C. for 1 h before it was warmed to 25° C. over 1 h. To the mixture was added 10% NH$_4$OH (10 mL) and dichloromethane (10 mL). The aqueous layer was further extracted with dichloromethane (10 mL×2). The combined dichloromethane solution was washed with brine (10 mL), dried over sodium sulfate, concentrated, and purified by silica gel column chromatography (DCM:THF 3:1 to 2:1) to provide 7a (93 mg, 0.22 mmol, 60%) as white solid. $^1$HNMR (400 MHz, CDCl$_3$): δ=7.63 (m, 2H), 7.33 (t, J=8.4 Hz, 2H), 7.05 (dt, J=7.4, 2.0 Hz, 2H), 6.47 (dd, J=8.3, 3.0 Hz, 2H), 5.22 (t, J=3.5 Hz, 2H), 1.23 (d, J=16.0 Hz, 18H); $^{31}$PNMR (162 MHz, CDCl$_3$): δ=61.8 Hz; $^{13}$CNMR (100 MHz, CDCl$_3$): δ=163.9 (m), 134.6, 129.1 (t, J=3.3 Hz), 122.0 (t, J=4.7 Hz), 113.5 (t, J=2.7 Hz), 113.5 (d, J=94.8 Hz), 72.4 (dd, J=64.8, 9.0 Hz), 33.5 (dd, J=37.9, 5.4 Hz), 23.3. ESI-MS: m/z 419 [M+H]$^+$.

Example 7: Preparation of (2S,2'S,3S,3'S)-3,3'-di-tert-butyl-2,2',3,3'-tetrahydro-2,2'-bibenzo[d][1,3]oxaphosphole bisoxide (8a). To a solution of 7a (70 mg, 0.17 mmol, 1 equiv), triethylamine (169 mg, 1.7 mmol, 10 equiv) in toluene (10 mL) at 25° C. was added trichlorosilane (114 mg, 0.84 mmol, 5 equiv). The mixture was heated to 80° C. and stirred under nitrogen for 12 h. To the mixture at 0° C. was added degassed 30% NaOH (10 mL) over 5 min. The resulting mixture was stirred at 60° C. for about 1 h until the two layers became clear. The toluene layer was separated under N$_2$ and the aqueous layer was further extracted with toluene twice (5 mL×2). The combined toluene was dried over Na$_2$SO$_4$, concentrated under N$_2$, and purified by passing through a neutral alumina plug (eluent: hexanes/ether 1/1) to provide 8a (60 mg, 0.155 mmol, 93%) as white solid. $^1$HNMR (400 MHz, CD$_2$Cl$_2$): δ=7.43 (m, 2H), 7.26 (m, 2H), 7.94 (m, 2H), 6.83 (d, J=8.2 Hz, 2H), 5.01 (t, J=3.2 Hz, 2H), 0.95 (d, J=12.8 Hz, 18H); $^{31}$PNMR (162 MHz, CD$_2$Cl$_2$): δ=−1.5; $^{13}$CNMR (100 MHz, CD$_2$Cl$_2$): δ=163.9, 131.6 (t, J=10.4 Hz), 131.5, 122.6 (t, J=5.1 Hz), 121.4 (t, J=3.2 Hz), 111.6, 85.8 (dd, J=70.5, 64.3 Hz), 31.0 (t, J=9.1 Hz), 26.9 (t, J=7.5 Hz).

Example 8: Preparation of Rh[(2S,2'S,3S,3'S)—BIBOP (nbd)]BF$_4$ (9a) To a mixture of Rh(nbd)$_2$BF$_4$ (40.1 mg, 0.11 mmol, 0.9 equiv) in THF (0.5 mL) at 0° C. was added a solution of 8a (46 mg, 0.12 mmol, 1.0 equiv) in THF (0.5 mL). The mixture was stirred at 25° C. for 0.5 h, then concentrated to about 0.5 mL. Ether (10 mL) was added, the mixture was stirred at 25° C. for 10 min, and filtered under N$_2$ to provide 9a (70 mg, 0.104 mmol, 88%) as a red solid. $^1$HNMR (400 MHz, CD$_2$Cl$_2$): δ=7.62 (t, J=6.3 Hz, 2H), 7.54 (t, J=7.4 Hz, 2H), 7.24 (td, J=7.5, 1.7 Hz, 2H), 7.04 (d, J=8.2 Hz, 2H), 5.97 (m, 4H), 5.41 (dd, J=22.9, 1.2 Hz, 2H), 4.25 (br s, 2H), 1.93 (br s, 2H), 0.99 (d, J=16.1 Hz, 18H); $^{31}$PNMR (162 MHz, CD$_2$Cl$_2$): δ=85.8 (dd, J=152.6, 6.5 Hz); $^{13}$CNMR (100 MHz, CD$_2$Cl$_2$): δ=161.1 (d, J=3.0 Hz), 134.8, 130.7 (t, J=4.7 Hz), 124.2 (t, J=4.2 Hz), 114.8 (m), 113.8, 92.2 (m), 87.6 (td, J=22.4, 3.3 Hz), 86.6 (dd, J=10.3, 5.7 Hz), 73.0 (m), 56.7 (d, J=1.5 Hz), 35.9 (m), 26.5 (t, J=2.5 Hz).

Examples 9-12

Examples 9-12 describe the preparation of preparation of (Rh[(2S,2'S,3S,3'S)-MeO-BIBOP(nbd)]BF$_4$ (9b) as depicted below:

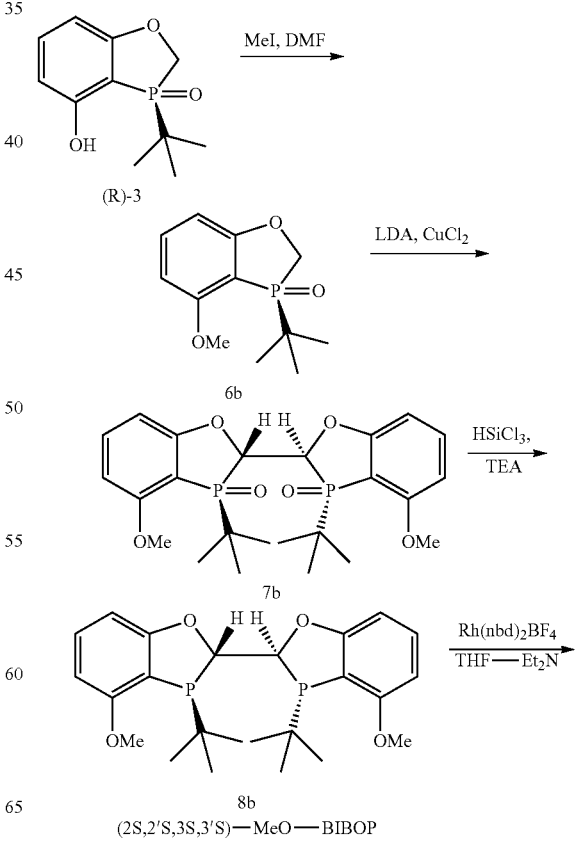

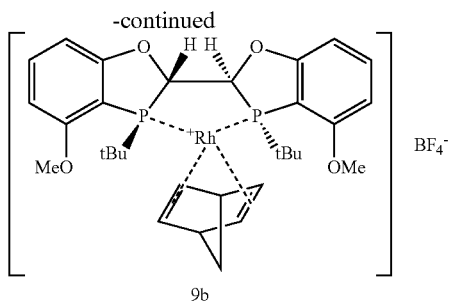

9b

Example 9: Preparation of (R)-3-tert-butyl-4-methoxy-2,3-dihydrobenzo[d][1,3]oxaphosphole oxide (6b). To a suspension of 3 (170 mg, 0.752 mmol) and potassium carbonate (0.519 g, 3.76 mmol, 5 equiv) in DMF (5 mL) at 25° C. was added MeI (0.32 g, 2.26 mmol, 3 equiv). The mixture was stirred at 25° C. for 12 h, then quenched with water (5 mL) and Me-THF (20 mL). The water layer was washed with Me-THF (10 mL). The combined Me-THF was washed with brine, dried over sodium sulfate, concentrated and purified by silica gel column chromatography (eluent: EtOAc/MeOH 4/1) to provide 6b (150 mg, 0.625 mmol, 83%) as white solid. $^1$HNMR (400 MHz, CDCl$_3$): δ=7.38 (t, J=8.2 Hz, 1H), 6.52 (dd, J=8.3, 3.0 Hz, 1H), 6.46 (dd, J=8.2, 4.2 Hz, 1H), 4.50 (dd, J=13.9, 2.3 Hz, 1H), 4.38 (dd, J=13.9, 10.4 Hz, 1H), 3.87 (s, 3H), 1.26 (d, J=16.4 Hz, 9H); $^{31}$PNMR (162 MHz, CDCl$_3$): δ=64.5; $^{13}$CNMR (100 MHz, CDCl$_3$): δ=166.6 (d, J=17.0 Hz), 161.3, 136.5, 106.4 (d, J=5.0 Hz), 103.1 (d, J=6.0 Hz), 102.5 (d, J=92.0 Hz), 66.0 (d, J=59.0 Hz), 55.6, 33.6 (d, J=73.0 Hz), 24.5; ESI-MS: m/z 241 [M+H]$^+$.

Example 10: Preparation of ((2S,2'S,3R,3'R)-3,3'-di-tert-butyl-4,4'-dimethoxy-2,2',3,3'-tetrahydro-2,2'-bibenzo[d][1,3]oxaphosphole bisoxide (7b). To a solution of 6b (150 mg, 0.624 mmol) in THF (5 mL) at −78° C. was added 1.8 M LDA (0.416 mL, 0.749 mmol, 1.2 equiv) over 5 min. The mixture was stirred at −78° C. for 1 h before the addition of anhydrous CuCl$_2$ (253 mg, 1.87 mmol, 3 equiv) in one portion. The resulting mixture was stirred at −78° C. for 1 h before it was warmed to 25° C. over 1 h. To the mixture was added 10% NH$_4$OH (10 mL) and dichloromethane (10 mL). The aqueous layer was further extracted with dichloromethane (5 mL). The combined dichloromethane solution was washed with brine (10 mL), dried over sodium sulfate, concentrated, and purified by silica gel column chromatography (eluent: EtOAc to EtOAc/MeOH 3/2) to provide 7b (100 mg, 0.21 mmol, 67%) as a white solid. $^1$HNMR (400 MHz, CD$_2$Cl$_2$): δ=7.32 (t, J=8.2 Hz, 1H), 6.53 (dd, J=8.2, 3.9 Hz, 1H), 6.19 (dd, J=8.3, 2.6 Hz, 1H), 5.14 (m, 1H), 3.92 (s, 3H), 1.25 (d, J=16.2 Hz, 9H); $^{31}$PNMR (162 MHz, CD$_2$Cl$_2$): δ=60.9; $^{13}$CNMR (100 MHz, CD$_2$Cl$_2$): δ=166.3 (t, J=7.9 Hz), 161.7, 136.8, 106.5 (t, J=2.6 Hz), 104.1 (t, J=2.8 Hz), 102.7 (dd, J=96.9, 4.9 Hz), 73.31 (m), 56.2, 34.5 (m), 24.5; ESI-MS: m/z 479 [M+H]$^+$.

Example 11: (2S,2'S,3S,3'S)-3,3'-di-tert-butyl-4,4'-dimethoxy-2,2',3,3'-tetrahydro-2,2'-bibenzo[d][1,3]oxaphosphole (8b). To a solution of 7b (100 mg, 0.209 mmol) and triethylamine (422 mg, 4.18 mmol, 20 equiv) in toluene (10 mL) was added trichlorosilane (283 mg, 2.09 mmol, 10 equiv). The mixture was heated to 80° C. for 12 h, then cooled to 0° C. and quenched with addition of degassed 30% NaOH solution (5 mL) over 5 min. The mixture was further stirred at 60° C. for about 1 h until the two layers became clear. The toluene layer was separated under N$_2$ and the aqueous layer was further extracted with toluene twice (5 mL×2). The combined toluene solution was dried over sodium sulfate, concentrated under N$_2$, and purified by passing through a neutral alumina plug (eluent: hexanes/ether 5/1) to provide 8b (70 mg, 0.157 mmol, 75%) as a white solid. $^1$HNMR (500 MHz, CD$_2$Cl$_2$): δ=7.22 (t, J=8.2 Hz, 2H), 6.50 (d, J=8.2 Hz, 2H), 6.48 (m, 2H), 4.93 (t, J=3.0 Hz, 2H), 3.83 (s, 6H), 0.98 (d, J=12.7 Hz, 18H); $^{31}$PNMR (202 MHz, CD$_2$Cl$_2$): δ=−5.3; $^{13}$CNMR (125 MHz, CD$_2$Cl$_2$): δ=165.4, 162.3 (t, J=6.2 Hz), 132.8, 110.0 (t, J=5.9 Hz), 104.9, 103.3, 86.3 (m), 55.9, 32.6 (m), 27.7 (t, J=7.3 Hz).

Example 12: Preparation of Rh[(2S,2'S,3S,3'S)-MeO-BIBOP(nbd)]BF$_4$ (9b) To a mixture of Rh(NBD)$_2$BF$_4$ (37.7 mg, 0.10 mmol, 0.9 equiv) in THF (0.1 mL) at 0° C. was added a solution of 8b (50 mg, 0.11 mmol, 1.0 equiv) in THF (0.5 mL). The mixture was stirred at 25° C. for 0.5 h before ether (10 mL) was added. After stirred at 25° C. for 10 min, the mixture was filtered under N$_2$ to provide 9b (60 mg, 0.082 mmol, 73%) as a red solid. $^1$HNMR (400 MHz, CD$_2$Cl$_2$): δ=7.49 (t, J=8.2 Hz, 2H), 6.74 (dd, J=7.6, 3.4 Hz, 2H), 6.66 (d, J=8.0 Hz, 2H), 6.31 (br s, 2H), 6.07 (br s, 2H), 5.36 (m, 2H), 4.24 (br s, 2H), 4.04 (s, 6H), 1.96 (br s, 2H), 1.04 (d, J=16.0 Hz, 18H); $^{31}$PNMR (162 MHz, CD$_2$Cl$_2$): δ=84.0 (dd, J=155.2, 4.9 Hz); ESI-MS: m/z 557 [M-BF$_4^-$]$^+$; $^{13}$CNMR (100 MHz, CD$_2$Cl$_2$): δ=162.7, 161.3 (t, J=3.0 Hz), 136.1, 106.5, 105.4 (t, J=2.0 Hz), 103.7 (m), 91.7 (dd, J=11.2, 5.0 Hz), 89.3 (dd, J=10.2, 4.6 Hz), 88.9 (td, J=23.3, 3.2 Hz), 72.6 (m), 56.4, 56.1, 37.3, 27.0 (t, J=2.7 Hz).

Examples 13-16

Examples 13-16 describe the preparation of preparation of Rh[(2S,2'S,3S,3'S)—BIBOP(nbd)]BF$_4$ (9c) as depicted below:

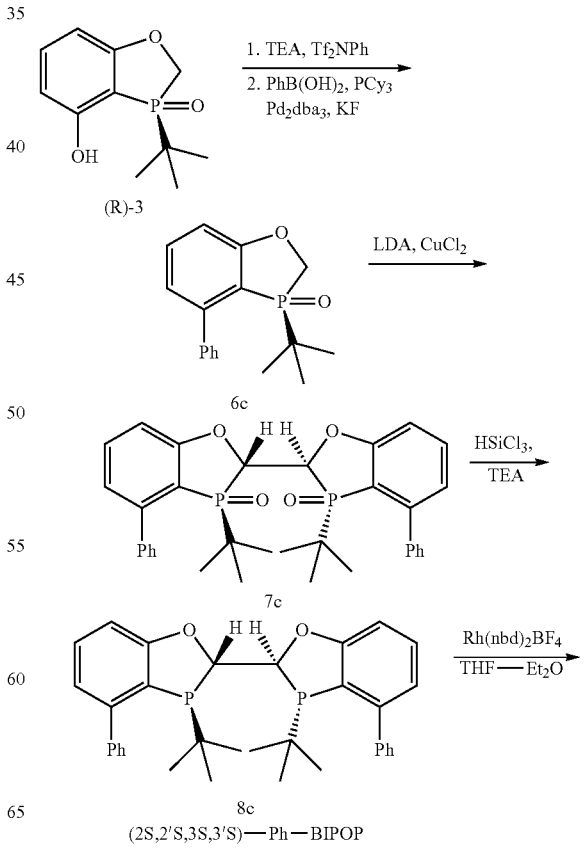

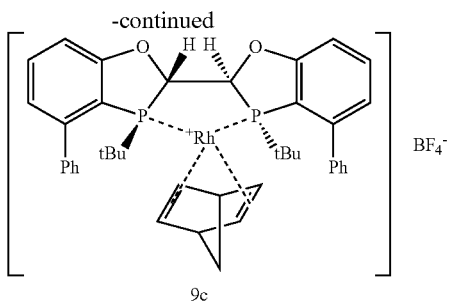

9c

Example 13: Preparation of (R)-3-tert-butyl-4-phenyl-2,3-dihydrobenzo[d][1,3]oxaphosphole. To a mixture of (R)-3 chiral triflate (2.0 g, 5.58 mmol) (prepared as described in Example 5), phenylboronic acid (1.02 g, 8.37 mmol, 1.5 equiv), Pd$_2$dba$_3$ (153 mg, 0.17 mmol, 3 mol %), PCy$_3$ (0.31 g, 1.12 mmol, 20 mol %), and potassium fluoride (1.30 g, 23.3 mmol, 4.0 equiv) was charged degassed dioxane (30 mL). The mixture was stirred at 100° C. under nitrogen for 24 h and then concentrated to remove most of dioxane. To the residue was added with dichloromethane (50 mL) and water (50 mL) and the mixture was filtered over a celite pad. The organic layer was separated, washed with brine, concentrated, and purified by silica gel column chromatography (eluent: hexane to EtOAc) to provide 6c as a white crystalline solid (1.5 g, 5.24 mmol, 94%). $^1$HNMR (400 MHz, CDCl$_3$): δ=7.76 (m, 2H), 7.35-7.53 (m, 4H), 7.05 (dd, J=7.5, 3.6 Hz, 1H), 6.91 (dd, J=8.3, 3.2 Hz, 1H), 4.56 (dd, J=13.9, 1.1 Hz, 1H), 4.44 (dd, J=13.8, 10.5 Hz, 1H), 0.78 (d, J=16.1 Hz, 9H); $^{31}$PNMR (162 MHz, CDCl$_3$): δ=65.1; $^{13}$CNMR (100 MHz, CDCl$_3$): δ=165.7 (d, J=19.0 Hz), 146.7 (d, J=6.0 Hz), 140.6 (d, J=2.0 Hz), 134.8 (d, J=2.0 Hz), 129.6, 128.5, 128.3, 123.5 (d, J=8.0 Hz), 112.6 (d, J=6.0 Hz), 112.4 (d, J=88.0 Hz), 65.3 (d, J=62.0 Hz), 33.8 (d, J=70 Hz), 33.9; ESI-MS: m/z 287 [M+H]$^+$.

Example 14: Preparation of (2S,2'S,3R,3'R)-3,3'-di-tert-butyl-4,4'-diphenyl-2,2',3,3'-tetrahydro-2,2'-bibenzo[d][1,3]oxaphosphole bisoxide (7c). Compound 7c was prepared as a white solid (43%) under similar conditions to those described for compound 7b in Example 10 except that compound 6c was used instead of compound 6b. $^1$HNMR (400 MHz, CDCl$_3$): δ=7.85 (d, J=10.9 Hz, 4H), 7.47 (t, J=7.2 Hz, 4H), 7.38 (dd, J=15.6, 8.0 Hz, 4H), 7.08 (dd, J=7.4, 2.6 Hz, 2H), 6.58 (dd, J=8.2, 2.3 Hz, 2H), 5.30 (m, 2H), 0.84 (d, J=15.9 Hz, 18H); $^{31}$PNMR (162 MHz, CDCl$_3$): δ=62.9; $^{13}$CNMR (100 MHz, CDCl$_3$): δ=164.9 (t, J=9.0 Hz), 146.2 (t, J=3.0 Hz), 140.4, 134.6, 129.8, 128.5, 128.3, 123.3 (t, J=4.0 Hz), 112.3 (t, J=3.0 Hz), 112.2 (dd, J=94.0, 4.7 Hz), 71.8 (m), 34.2 (m), 23.6; ESI-MS: m/z 571 [M+H]$^+$.

Example 15: Preparation of (2S,2'S,3S,3'S)-3,3'-di-tert-butyl-4,4'-diphenyl-2,2',3,3'-tetrahydro-2,2'-bibenzo[d][1,3]oxaphosphole ((2S,2'S,3S,3'S)-Ph-BIBOP) (8c). Compound 8c was prepared as a white solid (84%) under similar conditions to those described for compound 8b in Example 11 except that compound 7c was used instead of compound 7b. $^1$HNMR (400 MHz, CD$_2$Cl$_2$): δ=7.71 (d, J=7.2 Hz, 4H), 7.41 (t, J=7.0 Hz, 4H), 7.25-7.36 (m, 4H), 6.99 (d, J=7.6 Hz, 2H), 6.79 (d, J=8.2 Hz, 2H), 5.07 (t, J=3.2 Hz, 2H), 0.70 (d, J=12.3 Hz, 18H); $^{31}$PNMR (162 MHz, CD$_2$Cl$_2$): δ=3.3; $^{13}$CNMR (100 MHz, CD$_2$Cl$_2$): δ=164.6, 146.3, 143.1, 131.8, 129.7 (t, J=2.0 Hz), 128.9, 128.0, 122.6, 110.5, 86.2 (d, J=4.0 Hz), 32.8 (t, J=10.0 Hz), 27.2 (t, J=7.0 Hz).

Example 16: Preparation of Rh[(2S,2'S,3S,3'S)-Ph-BIBOP(nbd)]BF$_4$ (9c). Metal complex 9c was prepared as yellow-red solid (85%) under similar conditions to those described in Example 12 for compound 9b except that except that compound 8d was used instead of compound 8b: $^1$HNMR (500 MHz, CD$_2$Cl$_2$): δ=7.68 (t, J=7.4 Hz, 4H), 7.59 (dd, J=13.5, 6.4 Hz, 4H), 7.54 (d, J=7.8 Hz, 4H), 7.19 (d, J=8.3 Hz, 2H), 6.99 (d, J=7.3 Hz, 2H), 5.61 (s, 2H), 5.09 (s, 2H), 3.79 (s, 2H), 3.65 (s, 2H), 1.51 (s, 2H), 0.86 (d, J=15.6 Hz, 18H); $^{31}$PNMR (202 MHz, CD$_2$Cl$_2$): δ=46.8 (d, $^2$J$_{RhP}$=154 Hz); $^{13}$CNMR (125 MHz, CD$_2$Cl$_2$): δ=162.2, 147.9, 142.6, 134.8, 130.1, 139.7, 129.4, 126.7 (d, J=2.5 Hz), 113.8, 94.1, 86.9 (t, J=26.8 Hz), 83.4, 71.9, 56.8, 36.9, 26.3.

Examples 17-20

Examples 17-20 describe the preparation of Rh[(2S,2'S,3S,3'S)-Me-BIBOP(nbd)]BF$_4$ (9d) as depicted in below:

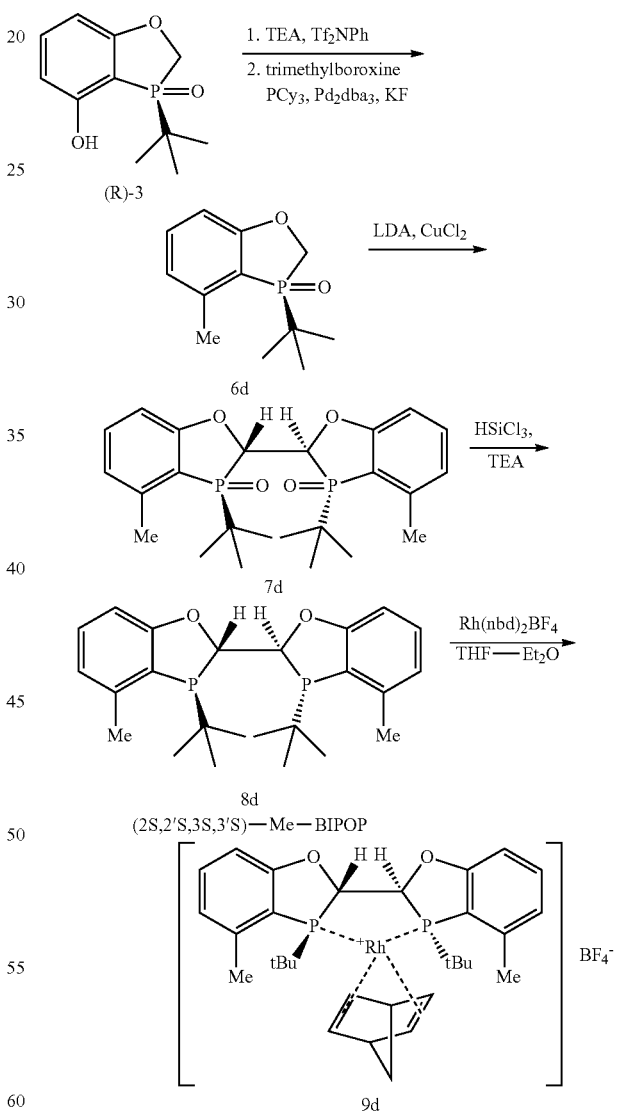

Example 17: Preparation of (R)-3-tert-butyl-4-methyl-2,3-dihydrobenzo[d][1,3]oxaphosphole (6d). To a mixture of (R)-3 chiral triflate (0.5 g, 1.4 mmol) (prepared as described in Example 5), trimethylboroxine (0.21 g, 1.7 mmol, 1.2 equiv), Pd$_2$dba$_3$ (38 mg, 0.042 mmol, 3 mol %), PCy$_3$ (0.078 g, 0.28 mmol, 20 mol %), and potassium fluoride (0.33 g, 5.6 mmol, 4.0 equiv) was charged degassed dioxane (10 mL). The mixture was stirred at 100° C. under nitrogen for 24 h and then concentrated to remove most of dioxane. To the residue was added dichloromethane (15 mL) and water (15 mL) and the mixture was filtered over a celite pad. The organic layer was separated, washed with brine, concentrated, and purified by silica gel column chromatography (eluent: hexane to EtOAc) to provide 6d as a white crystalline solid (0.2 g, 0.89 mmol, 64%). $^1$HNMR (500 MHz, CDCl$_3$): δ=7.32 (t, J=7.9 Hz, 1H), 6.83 (dd, J=7.4, 3.4 Hz, 1H), 6.72 (dd, J=8.3, 3.4 Hz, 1H), 4.56 (d, J=13.7 Hz, 1H), 4.33 (dd, J=13.7, 10.4 Hz, 1H), 2.57 (s, 3H), 1.22 (d, J=15.9 Hz, 9H); $^{31}$PNMR (202 MHz, CDCl$_3$): δ=65.2; $^{13}$CNMR (125 MHz, CDCl$_3$): δ=165.1 (d, J=20.0 Hz), 142.0 (d, J=7.5 Hz), 134.7 (d, J=2.5 Hz), 123.8 (d, J=8.8 Hz), 112.5 (d, J=91.3 Hz), 111.0 (d, J=5.0 Hz), 65.4 (d, J=60.0 Hz), 34.2 (d, J=70.0 Hz), 24.2 (d, J=1.4 Hz), 20.7 (d, J=2.8 Hz); ESI-MS: m/z 225 [M+H]$^+$.

Example 18: Preparation of (2S,2'S,3R,3'R)-3,3'-di-tert-butyl-4,4'-dimethyl-2,2',3,3'-tetrahydro-2,2'-bibenzo[d][1,3]oxaphosphole bisoxide (7d). Compound 7d was prepared as a white solid (74%) under similar conditions to those described for compound 7b in Example 10 except that compound 6d was used instead of compound 6b. $^1$HNMR (500 MHz, CDCl$_3$): δ=7.10 (t, J=7.9 Hz, 2H), 6.76 (dd, J=7.4, 2.4 Hz, 2H), 6.10 (dd, J=8.2, 2.4 Hz, 2H), 5.14 (m, 2H), 2.56 (s, 6H), 1.20 (d, J=15.7 Hz, 18H); $^{31}$PNMR (202 MHz, CDCl$_3$): δ=63.2; $^{13}$CNMR (125 MHz, CDCl$_3$): δ=164.1 (t, J=8.8 Hz), 141.3 (t, J=2.5 Hz), 134.1, 123.6 (t, J=3.8 Hz), 112.3 (d, J=93.8 Hz), 110.7 (t, J=2.5 Hz), 72.6 (m), 34.4 (m), 23.9, 20.5 (t, J=1.3 Hz); ESI-MS: m/z 447 [M+H]$^+$.

Example 19: Preparation of (2S,2'S,3S,3'S)-3,3'-di-tert-butyl-4,4'-dimethyl-2,2',3,3'-tetrahydro-2,2'-bibenzo[d][1,3]oxaphosphole ((2S,2'S,3S,3'S)-Me-BIB OP, 8d). Compound 8d was prepared as a white solid (86%) under similar conditions to those described for compound 8b in Example 11 except that compound 7d was used instead of compound 7b. HNMR (500 MHz, CD$_2$Cl$_2$): δ=7.13 (t, J=7.8 Hz, 2H), 6.78 (d, J=7.3 Hz, 2H), 6.61 (d, J=8.0 Hz, 2H), 4.89 (t, J=2.5 Hz, 2H), 2.48 (s, 6H), 0.98 (d, J=12.4 Hz, 18H); $^{31}$PNMR (202 MHz, CD$_2$Cl$_2$): δ=−6.2; $^{13}$CNMR (125 MHz, CD$_2$Cl$_2$): δ=164.1, 142.2 (t, J=8.8 Hz), 131.4, 122.9 (t, J=1.9 Hz), 122.3 (m), 108.9 (t, J=0.9 Hz), 85.9 (m), 33.1 (m), 27.8 (t, J=6.3 Hz), 23.3 (t, J=3.8 Hz).

Example 20: Preparation of Rh[(2S,2'S,3S,3'S)-Me-BI-BOP(nbd)]BF$_4$ (9d). Metal complex 9d was prepared as a yellow-red solid (85%) under similar conditions to those described in Example 12 for compound 9b except that compound 8d was used instead of compound 8b. $^1$HNMR (500 MHz, CD$_2$Cl$_2$): δ=7.42 (t, J=7.8 Hz, 2H), 7.03 (dd, J=7.1, 2.2 Hz, 2H), 6.91 (d, J=8.2 Hz, 2H), 5.96 (s, 2H), 5.93 (s, 2H), 5.21 (d, J=8.7 Hz, 2H), 4.29 (s, 2H), 2.69 (s, 6H), 1.98 (s, 2H), 0.96 (d, J=15.6 Hz, 18H); (202 MHz, CD$_2$Cl$_2$): δ=71.6 (d, $^2J_{RhP}$=152 Hz); $^{13}$CNMR (125 MHz, CD$_2$Cl$_2$): δ=162.3, 141.6 (t, J=5.0 Hz), 134.9 (d, J=6.3 Hz), 115.5 (d, J=32.5 Hz), 111.7 (t, J=1.8 Hz), 89.9 (m), 88.7 (m), 73.4 (m), 55.9 (d, J=1.4 Hz), 37.6 (m), 27.2 (d, J=2.5 Hz), 25.2 (d, J=4.6 Hz).

Examples 21-23

Examples 21-23 describe the preparation of Rh[(2S,3R)-3-tert-butyl-2-(di-tert-butylphosphino)-4-methoxy-2,3-dihydrobenzo[d][1,3]oxaphosphole (nbd)]BF$_4$ (10c) as depicted below:

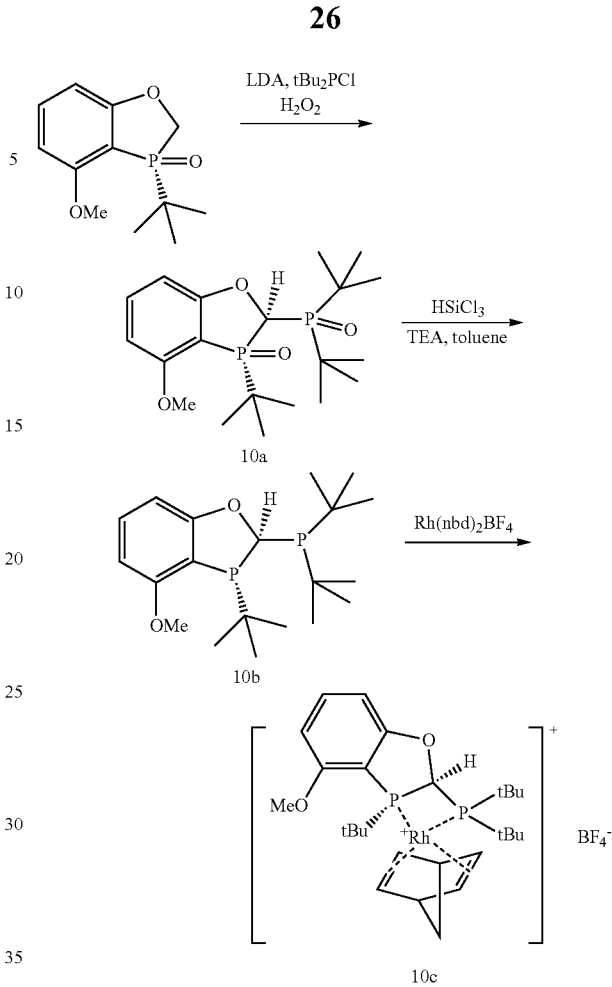

Example 21: Preparation of (2S,3S)-3-tert-butyl-2-(di-tert-butylphosphino)-4-methoxy-2,3-dihydrobenzo[d][1,3]oxaphosphole bisoxide (10a). To a solution of (S)-3-tert-butyl-4-methoxy-2,3-dihydrobenzo[d][1,3]oxaphosphole oxide (100 mg, 0.42 mmol) prepared using procedure described in Example 4, in THF (3 mL) at −78° C. was added LDA (0.24 mL, 1.8 mol/L, 0.46 mmol, 1.1 equiv). The mixture was stirred at −78° C. for 1 h before tBu$_2$PCl (90 mg, 0.50 mmol, 1.2 equiv) was added. The resulting mixture was further stirred at −78° C. for 1 h then allowed to warm to 25° C. over 1 h. To the mixture at 0° C. was added 30% H$_2$O$_2$ solution (94 mg, 0.83 mmol, 2.0 equiv). The resulting mixture was stirred at 25° C. for 1 h then quenched with water (5 mL) and dichloromethane (5 mL). The dichloromethane layer was dried and purified by column chromatography (eluent: EtOAc to EtOAc/MeOH 3/2) to provide 10a as a thick oil (120 mg, 0.30 mmol, 72%). $^1$HNMR (400 MHz, CD$_2$Cl$_2$): δ=7.45 (t, J=8.2 Hz, 1H), 6.57 (m, 2H), 4.90 (dd, J=9.0, 3.5 Hz, 1H), 3.90 (s, 3H), 1.41 (d, J=13.5 Hz, 9H), 1.32 (d, J=7.3 Hz, 9H), 1.28 (d, J=9.4 Hz, 9H); $^{31}$PNMR (162 MHz, CDCl$_3$): δ=61.7 (d, $^3J_{PP}$=9.8 Hz), 60.9 (d, $^3J_{PP}$=9.8 Hz); $^{13}$CNMR (100 MHz, CD$_2$Cl$_2$): δ=171.1, 164.8 (dd, J=14.4, 5.8 Hz), 161.6 (d, J=2.3 Hz), 136.7, 106.3 (d, J=5.2 Hz), 104.1 (d, J=5.6 Hz), 71.3 (dd, J=52.4, 43.0 Hz), 56.0, 37.9 (dd, J=55.7, 3.3 Hz), 37.0 (d, J=57.0 Hz), 35.0 (d, J=76.5 Hz), 27.7, 26.5, 25.9; ESI-MS: m/z 401 [M+H]$^+$.

Example 22: Preparation of (2S,3R)-3-tert-butyl-2-(di-tert-butylphosphino)-4-methoxy-2,3-dihydrobenzo[d][1,3]oxaphosphole (10b). To a solution of 10a (0.12 g, 0.30 mmol)

in toluene (10 mL) at 25° C. under nitrogen was added triethylamine (0.61 g, 5.99 mmol, 20 equiv) and trichlorosilane (0.41 g, 2.99 mmol). The mixture was heated to 120° C. for 12 h. To the mixture at 0° C. was added degassed 30% NaOH (10 mL) over 5 min. The resulting mixture was stirred at 60° C. for about 1 h until the two layers became clear. The toluene layer was separated under $N_2$ and the aqueous layer was further extracted with toluene twice (5 mL×2). The combined toluene extracts was dried over $Na_2SO_4$, concentrated under $N_2$, and purified by passing through a neutral alumina plug (eluent: hexanes/ether 5:1) to provide 10b (0.1 g, 0.27 mmol, 90%) as white solid. $^{31}$PNMR (162 MHz, $CD_2Cl_2$): δ=52.0 (d, $^3J_{PP}$=145.8 Hz), 9.4 (d, $^3J_{PP}$=146.7 Hz)

Example 23: Preparation of Rh[(2S,3R)-3-tert-butyl-2-(di-tert-butylphosphino)-4-methoxy-2,3-dihydrobenzo[d][1,3]oxaphosphole (nbd)]BF$_4$ (10c). To a suspension of Rh(NBD)$_2$BF$_4$ (46 mg, 0.122 mmol) in THF (0.5 mL) was added a solution of 10b (50 mg, 0.136 mmol, 1.1 equiv) in THF (0.5 mL). The mixture was stirred at 25° C. for 0.5 h, and then concentrated to about 1 mL. Degassed ether (10 mL) was added, the mixture was stirred at 25° C. for 10 min, and filtered under $N_2$ to provide 10c (60 mg, 0.092 mmol, 68%) as a yellow solid. $^1$HNMR (400 MHz, $CD_2Cl_2$): δ=7.49 (t, J=8.2 Hz, 1H), 6.71 (dd, J=8.3, 4.6 Hz, 1H), 6.64 (m, 2H), 6.10 (m, 1H), 5.97 (m, 1H), 5.83 (m, 1H), 5.74 (m, 1H), 4.27 (m, 2H), 3.98 (s, 3H), 1.77 (m, 2H), 1.50 (d, J=14.0 Hz, 9H), 1.18 (d, J=14.8 Hz, 9H), 1.10 (d, J=16.7 Hz, 9H); $^{31}$PNMR (162 MHz, $CD_2Cl_2$): δ=27.3 (dd, J=131.3, 39.2 Hz), 4.6 (dd, J=144.8, 39.2 Hz).

Examples 24-26

Examples 24-26 describe the preparation of Rh[(2S,3R)-3-tert-butyl-2-(di-tert-butylphosphino)-2,3-dihydrobenzo[d][1,3]oxaphosphole (nbd)]BF$_4$ (11c) as depicted below:

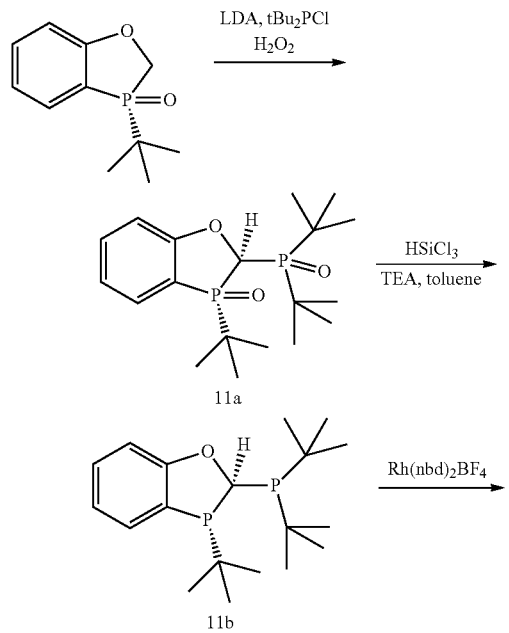

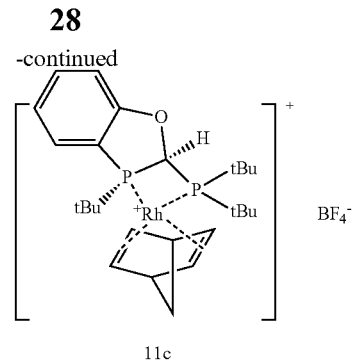

Example 24: Preparation of (2S,3S)-3-tert-butyl-2-(di-tert-butylphosphino)-2,3-dihydrobenzo[d][1,3]oxaphosphole bisoxide (11a). To a solution of (S)-3-tert-butyl-2,3-dihydrobenzo[d][1,3]oxaphosphole (0.5 g, 2.38 mmol) in THF (6 mL) was added LDA (1.45 mL, 1.8 M, 2.62 mol, 1.1 equiv) at −78° C. The mixture was stirred at −78° C. for 1 h before addition of chloro di-tert-butylphosphine (0.473 g, 2.62 mmol, 1.1 equiv) at −78° C. The resulting mixture was stirred at −78° C. for 15 min then warmed to 25° C. over 1 h. 30% $H_2O_2$ (0.54 g, 4.76 mmol, 2 equiv) was added and the mixture was further stirred at 25° C. for 1 h. 10% NaHSO$_3$ (10 mL) was added and the mixture was concentrated to remove most THF. DCM (20 mL) was added and the DCM layer was separated, dried over sodium sulfate and purified by column chromatography (eluent: EtOAc:MeOH=60:40) to provide 11a as a white solid (0.85 g, 2.30 mmol, 95%): $^1$HNMR (400 MHz, CDCl$_3$): δ=7.70 (dt, J=7.3, 1.0 Hz, 1H), 7.50 (t, J=7.4 Hz, 1H), 7.12 (dt, J=7.4, 2.7 Hz, 1H), 6.99 (dd, J=8.4, 3.2 Hz, 1H), 4.94 (dd, J=10.1, 3.8 Hz, 1H), 1.44 (d, J=13.5 Hz, 9H), 1.36 (d, J=14.6 Hz, 9H), 1.34 (d, J=16.1 Hz, 9H); $^{31}$PNMR (162 MHz, CDCl$_3$): δ=60.9 (d, $^3J_{PP}$=9.4 Hz), 60.0 (d, $^3J_{PP}$=9.3 Hz); $^{13}$CNMR (100 MHz, CDCl$_3$): δ=162.9, 134.7 (d, J=1.7 Hz), 129.8 (d, J=6.6 Hz), 122.7 (d, J=9.1 Hz), 114.9 (m), 113.6 (d, J=5.4 Hz), 70.8 (dd, J=51.8, 43.4 Hz), 37.6 (dd, J=55.8, 3.3 Hz), 36.7 (d, J=56.9 Hz), 34.6 (d, J=74.6 Hz), 27.3, 26.4, 25.1; ESI-MS: m/z 371 [M+H]$^+$.

Example 25: Preparation of (2S,3R)-3-tert-butyl-2-(di-tert-butylphosphino)-2,3-dihydrobenzo[d][1,3]oxaphosphole (11b). To a solution of 11a (0.64 g, 1.73 mmol) in toluene (10 mL) at 25° C. under nitrogen was added triethylamine (1.75 g, 17.3 mmol, 10 equiv) and trichlorosilane (1.40 g, 10.4 mmol, 6 equiv). The mixture was heated to 110° C. for 3 d. To the mixture at 0° C. was added degassed 30% NaOH (20 mL) over 5 min. The resulting mixture was stirred at 60° C. for about 1 h until the two layers became clear. The toluene layer was separated under $N_2$ and the aqueous layer was further extracted with toluene twice (10 mL×2). The combined toluene extracts was dried over $Na_2SO_4$, concentrated under $N_2$, and purified by passing through a neutral alumina plug (eluent: hexanes/ether 5:1) to provide 11b (0.5 g. 1.48 mmol, 85%) as a white solid. $^1$HNMR (400 MHz, $CD_2Cl_2$): δ=7.39 (m, 1H), 7.23 (t, J=7.3 Hz, 1H), 6.88 (m, 1H), 6.78 (d, J=8.2 Hz, 1H), 5.57 (t, J=5.3 Hz, 1H), 1.34 (d, J=11.0 Hz, 9H), 1.15 (d, J=11.1 Hz, 9H), 0.93 (d, J=12.2 Hz, 9H); $^{31}$PNMR (162 MHz, $CD_2Cl_2$): δ=52.0 (d, $^3J_{PP}$=146.1 Hz), 12.2 (d, $^3J_{PP}$=146.4 Hz).

Example 26: Preparation of Rh[(2S,3R)-3-tert-butyl-2-(di-tert-butylphosphino)-2,3-dihydrobenzo[d][1,3]oxaphosphole (nbd)]BF$_4$ (11c). To a suspension of Rh(NBD)$_2$BF$_4$ (0.27 g, 0.718 mmol) in THF (2 mL) was added a solution of 11b (0.27 g, 0.798 mmol, 1.1 equiv) in THF (2 mL). The mixture was stirred at 25° C. for 0.5 h, then concentrated to about 2 mL. Degassed ether (20 mL) was added, the mixture was stirred at 25° C. for 10 min, and filtered under $N_2$ to provide 11c (0.40 g, 0.645 mmol, 90%) as a yellow solid. $^1$HNMR (400 MHz, $CD_2Cl_2$): δ=7.61 (m, 1H), 7.56 (m, 1H), 7.23 (dt, J=6.6, 3.0 Hz, 1H), 6.71 (dd, J=6.1, 3.6 Hz, 1H), 5.97 (m, 1H), 5.88 (m, 2H), 5.78 (m, 1H), 4.30 (m, 1H), 4.28 (m, 1H), 1.78 (m, 2H), 1.52 (d, J=14.1 Hz, 9H), 1.18 (d, J=14.9 Hz, 9H), 1.03 (d, J=16.6 Hz, 9H); $^{31}$PNMR (162 MHz, $CD_2Cl_2$): δ=25.5 (dd, J=131.3, 40.0 Hz), 5.4 (dd, J=130.0, 41.1 Hz).

Example 27

Preparation of Rh[(2R,2'R,3R,3'R)—BIBOP(nbd)]$BF_4$.

The title compound was prepared in a manner similar to that described for the preparation of compound 9a in Examples 5-8 except that of (S)-3-tert-butyl-2,3-dihydrobenzo[d][1,3]oxaphosphol-4-ol oxide ((S)-3), was used in instead of (R)-3 (see Example 5). ((S)-3) was then reacted with the same reagents and in the same as described in Examples 6 and 7 to provide the bis-phosphine ligand (2R,2'R,3R,3'R)-3,3'-di-tert-butyl-2,2',3,3'-tetrahydro-2,2'-bibenzo[d][1,3]oxaphosphole bisoxide. The bis-phoshine ligand was then reacted with $Rh(bbd)_2BF_4$ in a manner similar to that described in Example 8 to provide the title compound.

An x-ray crystal structure of Rh[(nbd)((2R,2'R,3R,3'R)—BIBOP)]$BF_4$ (the H atoms are omitted) is shown in FIG. 1.

Example 28

Example 28 describes the use of the exemplary rhodium complex Rh[(nbd)((2R,2'R,3R,3'R)—BIBOP)]$BF_4$ (from Example 27) for hydrogenation of α-arylenamides, α-dehydroamino acid derivatives, β-(acetylamino)acrylates, and dimethyl itaconate

| Entry | Ar        | R      | ee [%] |
|-------|-----------|--------|--------|
| 1     | Ph        | Me     | 99     |
| 2     | p-MeO—Ph  | Me     | 99     |
| 3     | p-Br—Ph   | Me     | 99     |
| 4     | p-$CF_3$—Ph | Me   | >99    |
| 5     | m-Me—Ph   | Me     | >99    |
| 6     | 3-thiophenyl | Me  | >99    |
| 7     | 2-Naphthyl | Me    | 98     |
| 8     | p-Br—Ph   | $CF_3$ | 98     |
| 9     | p-MeO—Ph  | tBu    | 99     |

| Entry | Ar       | R            | R' | ee [%] |
|-------|----------|--------------|-----|--------|
| 1     | Ph       | tBu          | Me  | 99     |
| 2     | H        | Me           | Me  | >99    |
| 3     | Ph       | Me           | Me  | 97     |
| 4     | p-F—Ph   | Me           | Me  | 97     |
| 5     | p-MeO—Ph | Me           | Me  | 96     |
| 6     | m-Br—Ph  | Me           | Me  | 98     |
| 7     | o-Cl—Ph  | Me           | Me  | 97     |
| 8     | 2-thionyl | Me          | Me  | 99     |
| 9     | 2-naphthyl | Me         | Me  | 96     |
| 10    | Ph       | N-morpholine | Me  | 98     |
| 11    | Ph       | Me           | H   | 98     |

| Entry | R          | R'   | R''  | ee [%] | Config |
|-------|------------|------|------|--------|--------|
| 1     | H          | NHAc | Me   | 99     | R      |
| 2     | H          | Me   | NHAc | 99     | R      |
| 3     | $CH_2COOMe$ | H    | H    | 94     | S      |

The results of the study show that the exemplary metal complex of the invention Rh[(nbd)((2R,2R,3R,3'R)—BIBOP)]$BF_4$ is efficient for the enantioselective hydrogenation of α-arylenamides, α-dehydroamino acid derivatives, β-(acetylamino)acrylates, and dimethyl itaconate.

What is claimed is:
1. A compound of formula (Ia), (Ib), or a mixture thereof:

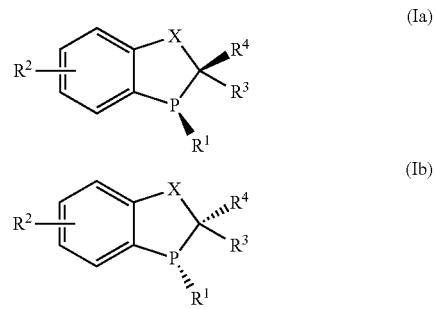

wherein:
X is O or S;
$R^1$ is —($C_1$-$C_6$)alkyl, —$CF_3$, —($C_3$-$C_{10}$)carbocyclyl, -(5- to 11-membered)heterocarbocyclyl, —($C_6$-$C_{10}$)aryl, -(5 to 11-membered)heteroaryl, or ferrocenyl; wherein said —($C_3$-$C_{10}$)carbocyclyl, -(5- to 11-membered)heterocarbocyclyl, —($C_6$-$C_{10}$)aryl and -(5 to 11-membered)heteroaryl of said $R^1$ is optionally substituted with 1 to 3 substituents independently selected from —O($C_1$-$C_6$)alkyl, —($C_1$-$C_6$)alkyl, and —$CF_3$;
$R^2$ is H, —O($C_1$-$C_6$)alkyl, —($C_1$-$C_6$)alkyl, —($C_3$-$C_{10}$)carbocyclyl, -(5- to 11-membered)heterocarbocyclyl, —($C_6$-$C_{10}$)aryl, -(5 to 11-membered)heteroaryl, —$NR^5R^6$, or —$SR^5$; wherein said —($C_3$-$C_{10}$)carbocyclyl, -(5- to 11-membered)heterocarbocyclyl, —($C_6$-$C_{10}$)aryl, and -(5 to 11-membered)heteroaryl of said $R^2$ is optionally substituted with 1 to 3 substituents independently selected from —O($C_1$-$C_6$)alkyl, —($C_1$-$C_6$)alkyl, and —$CF_3$;
$R^3$ is —$PR^7R^8$, —$CH_2PR^7R^8$, —$CH_2OPR^7R^8$, or a group of formula (A) or (B):

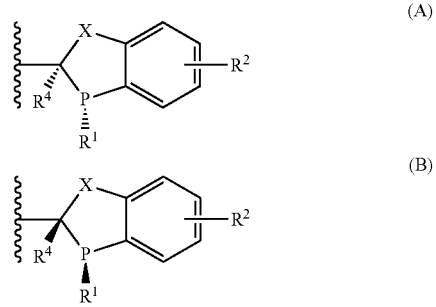

wherein X, $R^1$ and $R^2$ of the group of formula (A) or (B) are as defined above, and wherein the group of formula (A) only joins to the compound of formula (Ia), and the group of formula (B) only joins to the compound of formula (Ib);

$R^4$ is H, —$(C_1$-$C_6)$alkyl, —$(C_3$-$C_6)$cycloalkyl, -(3- to 6-membered)heterocycloalkyl, phenyl, (5- to 6-membered)heteroaryl, or —$SiR^5_3$; wherein said —$(C_1$-$C_6)$alkyl of said $R^4$ is optionally substituted with 1 to 3 substituents independently selected from —$O(C_1$-$C_6)$alkyl, —$(C_3$-$C_6)$cycloalkyl, phenyl, and -(5- to 6-membered)heteroaryl; and wherein said —$(C_3$-$C_6)$cycloalkyl, -(3- to 6-membered)heterocycloalkyl, phenyl, and (5- to 6-membered)heteroaryl of said $R^4$ is optionally substituted with 1 to 3 substituents independently selected from —$O(C_1$-$C_6)$alkyl, —$(C_1$-$C_6)$alkyl, and —$CF_3$;

$R^5$ and $R^6$ are each independently H, —$(C_1$-$C_6)$alkyl, —$CF_3$, —$(C_3$-$C_{10})$carbocyclyl, -(5- to 11-membered)heterocarbocyclyl, —$(C_6$-$C_{10})$aryl, or -(5 to 11-membered)heteroaryl; wherein each —$(C_1$-$C_6)$alkyl, —$CF_3$, —$(C_3$-$C_{10})$carbocyclyl, -(5- to 11-membered)heterocarbocyclyl, —$(C_6$-$C_{10})$aryl, and -(5 to 11-membered)heteroaryl of said $R^5$ and $R^6$ is optionally independently substituted with 1 to 3 substituents independently selected from halo, —$O(C_1$-$C_6)$alkyl, —$(C_1$-$C_6)$alkyl, and —$CF_3$; and $R^7$ and $R^8$ are each independently —$(C_1$-$C_6)$alkyl, —$CF_3$, —$(C_3$-$C_{10})$carbocyclyl, -(5- to 11-membered)heterocarbocyclyl, —$(C_6$-$C_{10})$aryl, -(5 to 11-membered)heteroaryl, or ferrocenyl; wherein said —$(C_3$-$C_{10})$carbocyclyl, -(5- to 11-membered)heterocarbocyclyl, —$(C_6$-$C_{10})$aryl and -(5 to 11-membered)heteroaryl of said $R^7$ and $R^8$ are each optionally independently substituted with 1 to 3 substituents independently selected from —$O(C_1$-$C_6)$alkyl, —$(C_1$-$C_6)$alkyl, and —$CF_3$.

2. The compound of claim 1 of formula (Ia), (Ib), or a mixture thereof, wherein X is O.

3. The compound of formula (Ia), (Ib), or a mixture thereof, according to claim 1, wherein $R^1$ is —$(C_1$-$C_6)$alkyl selected from —$CH_3$, —$CH_2CH_3$, —$CH(CH_3)_2$, —$C(CH_3)_3$, —$C(CH_2CH_3)_3$, or —$C(CH_2CH_3)(CH_3)_2$.

4. The compound of formula (Ia), (Ib), or a mixture thereof, according to claim 1, wherein $R^2$ is H, —$CH_3$ or —$OCH_3$.

5. The compound of formula (Ia), (Ib), or a mixture thereof, according to claim 1, wherein $R^4$ is —H.

6. The compound of formula (Ia), (Ib), or a mixture thereof, according to claim 1, $R^3$ is —$PR^7R^8$ or a group of formula (A).

7. The compound of formula (Ia), (Ib), or a mixture thereof, according to claim 1, wherein $R^1$ is —$C(CH_3)_3$; $R^2$ is —H, —$CH_3$, —$OCH_3$, or phenyl; and $R^3$ is —$PR^7R^8$.

8. The compound of formula (Ia), (Ib), or a mixture thereof, according to claim 7, wherein $R^7$ and $R^8$ are each —$C(CH_3)_3$ and X is O.

9. The compound of formula (Ia), according to claim 1, wherein $R^1$ is —$C(CH_3)_3$; $R^2$ is —H, —$CH_3$, —$OCH_3$, or phenyl; and $R^3$ is a group of formula (A).

10. The compound according to claim 1 having the formula (IIa), (IIb), or a mixture thereof:

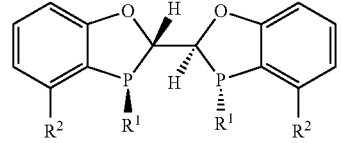

(IIa)

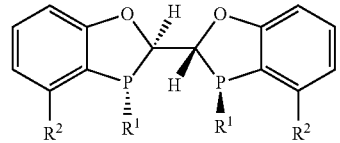

(IIb)

wherein $R^1$ is —$CH(CH_3)_2$, —$C(CH_3)_3$, —$C(CH_2CH_3)(CH_3)_2$, cyclohexyl, 1-adamantyl, phenyl, ortho-tolyl, 3,5-xylyl, ortho-anisyl, or ferrocenyl; and $R^2$ is H, —$OCH_3$, —$CH_3$, —$CF_3$, phenyl, or —$N(CH_3)_2$.

11. The compound according to claim 1 selected from:

(2S,2'S,3S,3'S)-3,3'-di-tert-butyl-2,2',3,3'-tetrahydro-2,2'-bibenzo[d][1,3]oxaphosphole, (2S,2'S,3S,3'S)-3,3'-di-tert-butyl-4,4'-dimethoxy-2,2',3, 3'-tetrahydro-2,2'-bibenzo[d][1,3]oxaphosphole, (2S,2'S,3S,3'S)-3,3'-di-tert-butyl-4,4'-diphenyl-2,2',3,3'-tetrahydro-2,2'-bibenzo[d][1,3]oxaphosphole, (2S,2'S,3S,3'S)-3,3'-di-tert-butyl-4,4'-dimethyl-2,2',3,3'-tetrahydro-2,2'-bibenzo[d][1,3]oxaphosphole, (2S,3R)-3-tert-butyl-2-(di-tert-butylphosphino-4-methoxy)-2,3-dihydrobenzo[d][1,3]oxaphosphole, and (2S,3R)-3-tert-butyl-2-(di-tert-butylphosphino)-2,3-dihydrobenzo[d][1,3]oxaphosphole.

12. A metal complex of formula (IVa), (IVb), (Va) or (Vb):

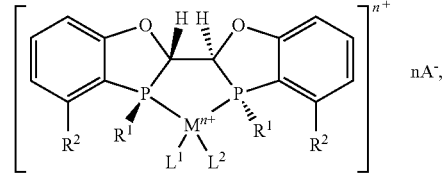

(IVa) $nA^-$,

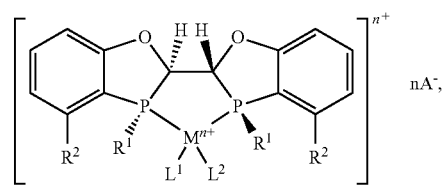

(IVb) $nA^-$,

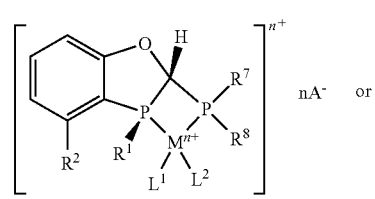

(Va) $nA^-$ or

-continued

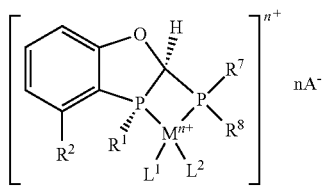

(Vb)

wherein
M is a transition metal selected from Co, Ni, Pd, Pt, Cu, Ag, Au, Ru, Fe, Rh and Ir;
A⁻ is a counter anion;
n is the oxidation state of the transition metal M;
L¹ and L² are each olefins, or L¹ and L² together represent a diolefin; and
X, R¹, R², R⁷, and R⁸ are as defined in claim 1.

13. The metal complex of claim 12, wherein M is Rh, A⁻ is BF₄⁻, and n is 1.

14. The metal complex of claim 12 selected from:
Rh[(2S,2'S,3S,3'S)-3,3'-di-tert-butyl-2,2',3,3'-tetrahydro-2,2'-bibenzo[d][1,3]oxaphosphole(nbd)]BF₄,
Rh[(2S,2'S,3S,3'S)-3,3'-di-tert-butyl-4,4'-dimethoxy-2,2',3,3'-tetrahydro-2,2'-bibenzo[d][1,3]oxaphosphole (nbd)]BF₄,
Rh[(2S,2'S,3S,3'S)-3,3'-di-tert-butyl-4,4'-diphenyl-2,2',3,3'-tetrahydro-2,2'-bibenzo[d][1,3]oxaphosphole(nbd)] BF₄,
Rh[(2S,2'S,3S,3'S)-3,3'-di-tert-butyl-4,4'-dimethyl-2,2',3,3'-tetrahydro-2,2'-bibenzo[d][1,3]oxaphosphole(nbd)] BF₄,
Rh[(2S,3R)-3-tert-butyl-2-(di-tert-butylphosphino)-4-methoxy-2,3-dihydrobenzo[d][1,3]oxaphosphole (nbd)]BF₄ and
Rh[(2S,3R)-3-tert-butyl-2-(di-tert-butylphosphino)-2,3-dihydrobenzo[d][1,3]-oxaphosphole(nbd)]BF₄.

15. A method of carrying out an asymmetric hydrogenation of a compound having a carbon-carbon or carbon-heteroatom double bond, the method comprising allowing said compound having a carbon-carbon or carbon-heteroatom double bond to react with hydrogen in the presence of a catalytic amount of the metal complex of claim 12.

16. The compound according to claim 1 having the formula (IIIa), (IIIb), or a mixture thereof:

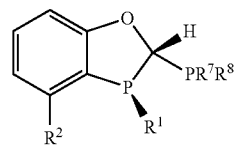

(IIIa)

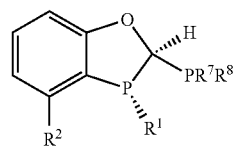

(IIIb)

wherein
R¹ is —CH(CH₃)₂, —C(CH₃)₃, —C(CH₂CH₃)(CH₃)₂, cyclohexyl, or 1-adamantyl;
R² is H, —OCH₃, —CH₃, —CF₃, phenyl, or —N(CH₃)₂; and
R⁷ and R⁸ are each —C(CH₃)₃.

* * * * *